(12) United States Patent
Blanchard

(10) Patent No.: US 12,297,411 B2
(45) Date of Patent: May 13, 2025

(54) AUTOMATED CELL CULTURE INCUBATORS COMPRISING SELECTIVELY PERMEABLE CELL CULTURE VESSEL STORAGE COMPARTMENTS

(71) Applicant: Thrive Bioscience, Inc., Beverly, MA (US)

(72) Inventor: Alan Blanchard, Topsfield, MA (US)

(73) Assignee: Thrive Bioscience, Inc., Beverly, MA (US)

( * ) Notice: Subject to any disclaimer, the term of this patent is extended or adjusted under 35 U.S.C. 154(b) by 248 days.

(21) Appl. No.: 17/316,672

(22) Filed: May 10, 2021

(65) Prior Publication Data

US 2021/0261899 A1 Aug. 26, 2021

Related U.S. Application Data

(62) Division of application No. 15/773,787, filed as application No. PCT/US2016/060710 on Nov. 4, 2016, now abandoned.

(60) Provisional application No. 62/251,035, filed on Nov. 4, 2015.

(51) Int. Cl.
| | |
|---|---|
| C12M 1/04 | (2006.01) |
| C12M 1/00 | (2006.01) |
| C12M 1/12 | (2006.01) |
| C12M 1/22 | (2006.01) |
| C12M 1/34 | (2006.01) |
| C12M 3/00 | (2006.01) |

(52) U.S. Cl.
CPC ............ *C12M 23/24* (2013.01); *C12M 1/22* (2013.01); *C12M 23/22* (2013.01); *C12M 23/44* (2013.01); *C12M 23/50* (2013.01); *C12M 37/04* (2013.01); *C12M 41/14* (2013.01); *C12M 41/36* (2013.01)

(58) Field of Classification Search
None
See application file for complete search history.

(56) References Cited

U.S. PATENT DOCUMENTS

| | | | |
|---|---|---|---|
| 4,033,825 A | 7/1977 | Haddad et al. | |
| 5,858,770 A | 1/1999 | Perlman | |
| 5,882,922 A * | 3/1999 | Tyndorf | C12M 29/04 435/325 |

(Continued)

FOREIGN PATENT DOCUMENTS

| | | | | |
|---|---|---|---|---|
| JP | 2006014675 A | * | 1/2006 | ............ C12M 23/42 |
| JP | 2007-097481 A | | 4/2007 | |

(Continued)

OTHER PUBLICATIONS

DuPont, Moisture Resistance of Tyvek® Is Superior to Medical-Grade Paper, Feb. 16, 2018, <https://www.dupont.co.za/news/tyvek-outperforms-paper.html>, retrieved Mar. 6, 2023 (Year: 2018).*

(Continued)

*Primary Examiner* — Holly Kipouros
(74) *Attorney, Agent, or Firm* — Wolf, Greenfield & Sacks, P.C.

(57) ABSTRACT

In some aspects, the invention relates to selectively permeable cell culture vessel storage containers and their methods of use. In some embodiments, the containers comprise a gas-permeable membrane that is selectively impermeable to water vapor.

9 Claims, 20 Drawing Sheets

(56) References Cited

U.S. PATENT DOCUMENTS

| | | | | |
|---|---|---|---|---|
| 5,958,762 | A | * | 9/1999 | Stoppini ................ C12M 25/02 435/297.5 |
| 2001/0024821 | A1 | * | 9/2001 | Potter .................... C12M 23/10 435/297.5 |
| 2003/0040104 | A1 | | 2/2003 | Barbera-Guillem |
| 2003/0228565 | A1 | * | 12/2003 | Oestreicher ........ G01N 15/1433 435/6.16 |
| 2004/0005699 | A1 | * | 1/2004 | Roos ..................... C12M 23/24 435/297.5 |
| 2004/0043481 | A1 | * | 3/2004 | Wilson .................. C12M 41/44 435/297.1 |
| 2006/0151185 | A1 | * | 7/2006 | Takagi ................... C12M 41/48 172/4 |
| 2007/0065936 | A1 | * | 3/2007 | Hasegawa .............. G02B 21/30 359/398 |
| 2007/0128715 | A1 | | 6/2007 | Vukasinovic et al. |
| 2010/0120136 | A1 | | 5/2010 | Larsen et al. |
| 2010/0151571 | A1 | | 6/2010 | Vukasinovic et al. |
| 2011/0107788 | A1 | | 5/2011 | Stahl et al. |
| 2012/0125936 | A1 | * | 5/2012 | Byers ..................... C12M 29/20 220/367.1 |
| 2013/0210123 | A1 | * | 8/2013 | Malcolm ................ C12M 21/06 435/285.1 |
| 2013/0295660 | A1 | | 11/2013 | Fey |
| 2016/0250632 | A1 | | 9/2016 | Hong et al. |
| 2018/0320122 | A1 | | 11/2018 | Blanchard |

FOREIGN PATENT DOCUMENTS

| | | |
|---|---|---|
| JP | 2008-259284 A | 10/2008 |
| WO | WO 2008-073313 A2 | 6/2008 |

OTHER PUBLICATIONS

Cutting et al., Establishing quality control in the new IVF laboratory, 2004, Human Fertility, 7(2):119-125 (Year: 2004).*

Document titled JP2006014675A Incubator and Culture Cassette Used for the Same, machine translation of JP 2006014675 provided by EPO, original document dated 2006 (Year: 2006).*

"Product description Box for microtiter plates", webpage cached by Internet Archive as early as Jul. 11, 2015 <http://www.infors-ht.com/index.php/de/produkte/schuettler/zubehoer-schuettler/box-fuer-mikrotiter-platten> (English machine translation provided by Google appended) (Year: 2015).*

Tominaga-Yoshino et al., "Suprachiasmatic Nucleus Cultures That Maintain Rhythmic Properties In Vitro", 2007, in Circadian Rhythms, pp. 481-492 (Year: 2007).*

Extended European Search Report mailed Jul. 26, 2019, in connection with Application No. EP16863119.0.

International Search Report and Written Opinion for Application No. PCT/US2016/060710 mailed Jan. 31, 2017.

International Preliminary Report on Patentability for Application No. PCT/US2016/060710 mailed May 17, 2018.

Potter et al., A new approach to neural cell culture for long-term studies. J Neurosci Methods. Sep. 30, 2001;110(1-2):17-24.

EP 16863119.0, Jul. 26, 2019, Extended European Search Report.

PCT/US2016/060710, Jan. 31, 2017, International Search Report and Written Opinion.

PCT/US2016/060710, May 17, 2018, International Preliminary Report on Patentability.

* cited by examiner

AUTOMATED CELL CULTURE INCUBATORS COMPRISING SELECTIVELY PERMEABLE CELL CULTURE VESSEL STORAGE COMPARTMENTS

RELATED APPLICATIONS

This Application is a divisional and claims the benefit under 35 U.S.C. § 120 of U.S. application Ser. No. 15/773,787, filed May 4, 2018 and entitled "AUTOMATED CELL CULTURE INCUBATORS COMPRISING SELECTIVELY PERMEABLE CELL CULTURE VESSEL STORAGE COMPARTMENTS", which is a National Stage filing under 35 U.S.C. § 371 of International Patent Application Serial No. PCT/US2016/060710, filed Nov. 4, 2016 and entitled "AUTOMATED CELL CULTURE INCUBATORS COMPRISING SELECTIVELY PERMEABLE CELL CULTURE VESSEL STORAGE COMPARTMENTS", which claims the benefit under 35 U.S.C. 119(e) of U.S. Provisional Application Ser. No. 62/251,035, filed Nov. 4, 2015 and entitled "AUTOMATED CELL CULTURE INCUBATORS COMPRISING SELECTIVELY PERMEABLE CELL CULTURE VESSEL STORAGE COMPARTMENTS", the entire contents of each of which are incorporated by reference herein.

FIELD

Aspects relate to cell culture incubators and to methods for using such incubators. Some aspects relate to methods for producing mammalian cell cultures in cell culture incubators.

BACKGROUND

Cell culture is a useful technique in both research and clinical contexts. However, maintenance of cell cultures (e.g., ex vivo mammalian cell cultures, tissue preparations, in vitro fertilization preparations, etc.) in available cell incubators is often a laborious process requiring highly trained personnel and stringent aseptic conditions. There is a need for improved cell culture incubators that enable long-term culture of cells under automated conditions with minimal human involvement.

SUMMARY

Improved cell culture incubators that enable long-term culture of cells under automated conditions with minimal human involvement have been developed. Such incubators provide automation and monitor equipment directly in an incubator cabinet to enable cells to be manipulated and monitored directly within the incubator cabinet. This avoids the need to remove cells from the incubator cabinet for manipulation and monitoring, which is desirable because removal from the incubator exposes cells to changes in surrounding temperature and gas conditions, which can alter cell growth and provide undesirable selection pressures.

It has been recognized herein that combining automation and monitoring equipment within the incubator cabinet poses certain challenges. One such challenge is the detrimental effect of humidified environments on electronic equipment. Generally, cell culture incubator cabinets maintain a humidified environment in order to prevent evaporation of cell culture media. Evaporation of cell culture media can lead to dysregulated cell culture component (e.g., salt, buffer, nutrient) concentrations and negatively impact cell culture.

Some aspects of the disclosure are based on a recognition that the use of humidified incubator cabinets for culturing mammalian cells poses at least two issues for electronic components (e.g., optics, sensors, computer controllers, and insulation covering the components). First, the high-humidity environment employed in currently used cell culture incubators can promote the growth of contaminants (e.g., microorganisms, such as mold and biofilm-forming bacteria) on electronic components. Second, condensation within humidified incubator cabinets may cause oxidation (e.g., rusting) of electronic equipment insulation, or malfunctioning of electronic components. Accordingly, new cell culture systems and methods are provided herein that permit the culture of mammalian cells (e.g., for autologous cell therapy or ex vivo cell therapy).

In some aspects, this document provides a container for enclosing a cell culture vessel, the container comprising a compartment having one or more walls configured to enclose a cell culture vessel within an interior, wherein each of the one or more walls is impermeable to gas and water vapor, and wherein the container comprises one or more access points (e.g., ports, openings, microchannels, etc.) configured to provide the appropriate gases and vapors (e.g., $CO_2$ and $H_2O$ vapor) to the interior of the container, thereby regulating the interior environment of the container.

In some aspects, this document provides a container for enclosing a cell culture vessel, the container comprising: a compartment having one or more walls configured to enclose a cell culture vessel within an interior, wherein a portion of at least one wall of the compartment comprises a gas permeable membrane that is selectively impermeable to water vapor.

In some embodiments, this document provides a plurality of containers as described by this document, wherein each container of the plurality is physically connected to at least one other container of the plurality. In some embodiments, the plurality of containers share a common wall comprising the gas permeable membrane. In some embodiments, the plurality comprises between about 2 and about 100 containers. In some embodiments, the plurality comprises at least 2, at least 3, at least 4, at least 5, at least 6, at least 7, at least 8, at least 9, at least 10, at least 15, at least 20, at least 30, at least 40, at least 50, at least 60, at least 70, at least 80, at least 90, or up to 100 containers.

In some embodiments, containers described by this document are located within a cell culture incubator. Thus, in some aspects this document provides a cell culture incubator comprising: an incubator cabinet comprising a temperature controlled internal chamber, and, one or more cell culture vessel containers, wherein each container comprises a compartment having one or more walls configured to enclose a cell culture vessel within a compartment interior, wherein a portion of at least one wall of the compartment comprises a gas permeable membrane that is selectively impermeable to water vapor.

In some aspects, this document provides a method for culturing cells, the method comprising: culturing cells in a within a cell culture vessel, wherein the cell culture vessel is present within a container, the container comprising a compartment having one or more walls configured to enclose the cell culture vessel within a compartment interior, wherein a portion of at least one wall of the compartment comprises a gas permeable membrane that is selectively impermeable to water vapor. In some embodiments, the container is present within the cell culture incubator.

In some embodiments, cell culture vessel containers described herein further comprise a cell culture vessel.

In some embodiments, the gas permeable membrane is permeable to $O_2$ and $CO_2$. In some embodiments, the gas permeable membrane has a thickness in a range of 0.1 µm to 200 µm. In some embodiments, the gas permeable membrane, which is selectively impermeable to water (e.g., liquid or vapor), comprises a polymer structure that permit transfer of gases but not water (e.g., liquid or vapor).

In some embodiments, the gas permeable membrane is hydrophobic. For example, in some embodiments, a gas permeable membrane comprises a halogenated compound or material (e.g., a molecule that contains halogen atoms, e.g., fluorine, chlorine, bromine, or iodine) that increases the hydrophobicity of the membrane. For example, in some embodiments, a gas permeable membrane is composed of polytetrafluoroethylene (PTFE), polyvinylidene fluoride (PVDF), polyethersulfone (PES), fluorinated ethylene-propylene (FEP). In some embodiments, the gas permeable membrane comprises a base material (e.g., may or may not be substantially hydrophobic) coated with a halogenated compound or material that increases the hydrophobicity of the membrane.

In some embodiments, the gas permeable membrane is connected to a support structure having one or more passages to the compartment interior wherein the gas permeable membrane covers the passages. In some embodiments, the gas permeable membrane is readily detachable from the support structure.

In some embodiments, at least one wall of the compartment comprises: a passage configured for removing from the compartment and/or introducing into the compartment a cell culture vessel; and, a moveable structure configured for opening and closing the passage. In some embodiments, the moveable structure comprises a seal configured to interface with a surface of the container that surrounds the passage. In some embodiments, the moveable structure comprises a hinge connected to the compartment and configured to permit the moveable structure to rotate between an open position to a closed position. In some embodiments, the moveable structure is configured to automatically transition between an open position to a closed position in response to an input signal from a remote control unit.

In some embodiments, the moveable structure is optically transparent. In some embodiments, each of the one or more walls are optically transparent.

In some embodiments, the container further comprises at least one exterior portion configured to interface with a second container.

In some embodiments, the container is a modular unit configured to physically interface with a plurality of other containers to form a rack of containers.

In some embodiments, the one or more containers are a plurality of containers, wherein the plurality comprises at least 2, at least 3, at least 4, at least 5, at least 6, at least 7, at least 8, at least 9, at least 10, at least 15, at least 20, at least 30, at least 40, at least 50, at least 60, at least 70, at least 80, at least 90, or up to 100 containers.

In some aspects, this document provides a cell culture container transfer device comprising a single rail crank-slider mechanism attached to two horizontally opposed, parallel arms, each arm comprising one or more grippers (e.g., pads) for contacting a microplate, wherein the transfer device is configured for removing a microplate from a cell culture container as described herein.

In some aspects, the disclosure provides a device for moving a multi-well culture plate, the device comprising: a support structure; a motor attached to the support structure, the motor comprising a rotor, a plate holder configured to translate along a longitudinal axis of a guide rail of the support structure, the plate holder comprises two, opposed arms extending parallel to the longitudinal axis of the guide rail, wherein each arm comprises one or more contact surfaces for engaging with the multi-well culture plate; a manipulator arm comprising a proximal region coupled to the rotor, a distal region coupled to the plate holder and an elbow positioned between the proximal region and distal region, wherein the manipulator arm is configured to convert torque imparted through the rotor to a translational force imparted on the plate holder to cause the plate holder to translate along longitudinal axis of a guide rail.

In some embodiments, the multi-well culture plate comprises a rectangular cuboidal body housing a plurality of cell culture wells, and wherein the set of contact surfaces are configured for interfacing with opposite vertical surfaces of the rectangular cuboidal body to hold the multi-well culture plate.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. Various embodiments of the invention will now be described, by way of example, with reference to the accompanying non-limiting drawings, in which:

FIG. 1A shows a schematic of an illustrative embodiment of a selectively permeable cell culture vessel storage container. FIG. 1B shows a schematic of an illustrative embodiment of a cell culture vessel; FIG. 1C shows a schematic of an illustrative embodiment of a selectively permeable cell culture vessel storage container housing a cell culture vessel.

FIG. 8A depicts a microplate resting on top of the feet and locators on the bottom surface of a selectively permeable cell culture vessel storage container. FIG. 8B depicts non-limiting embodiments of two selectively permeable cell culture vessel storage containers (e.g., having cross-sectional dimensions of 130 mm to 150 mm wide and 45 mm to 55 mm tall); the container on the top comprises feet on the bottom surface; the container on the bottom comprises feet and ribs. Non-limiting embodiments of side bond joints are also depicted in FIG. 8B.

FIG. 11A depicts attachment of a door seal to a first door frame. FIG. 11B depicts attachment of a selectively permeable membrane to a second door frame. FIG. 11C depicts assembly of a door comprising, in the following order, a door frame, seal, a selectively permeable membrane, and a second door frame. FIG. 11D depicts attachment of the assembled door to the walls of a container. FIGS. 11E and 11F depict epoxy on a membrane frame and attachment of the membrane frame to the container (e.g. support structure) depicted in FIG. 11D. FIG. 11G depicts a microplate placed inside the assembled selectively permeable cell culture vessel storage container.

FIG. 13A depicts a rear/side angle view of a transfer device; a selectively permeable cell culture vessel storage container is also depicted. FIG. 13B depicts a view of the transfer device described in FIG. 13A from a side angle. FIG. 13C depicts an illustrative embodiment of a transfer device. FIG. 13D is a schematic of an illustrative embodiment of a transfer device accessing the interior chamber of a selectively permeable cell culture vessel storage container. The transfer device pushes open the door of the container and places a microplate on the bottom surface of the container. In this schematic, the microplate contacts (e.g., rests on) the ribs and locators situated on the bottom surface (floor) of the container.

DETAILED DESCRIPTION

Figure 1A:
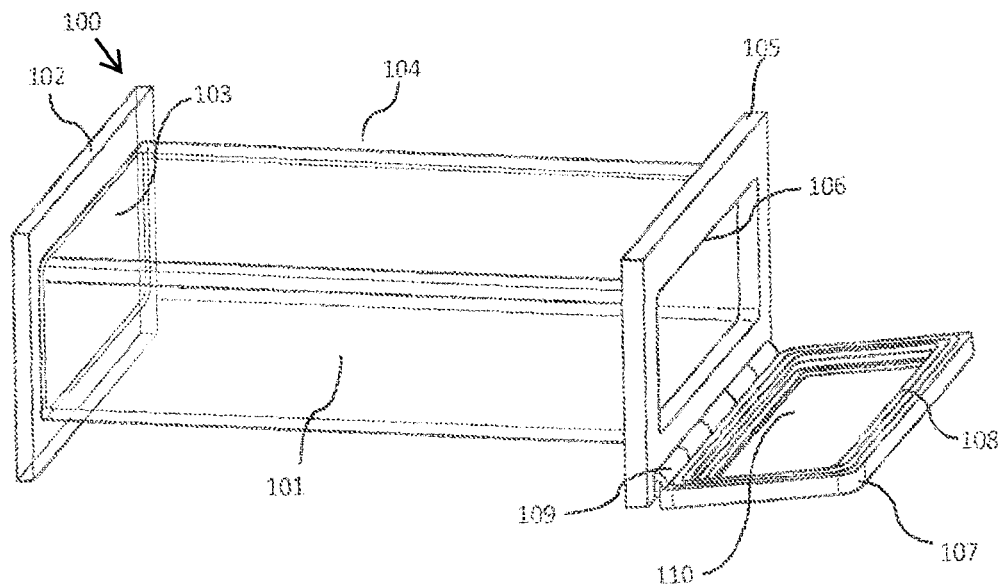
FIGS. 1A-1C are schematics of illustrative embodiments of a selectively permeable cell culture vessel storage container.

Currently used cell culture incubators impose barriers to the success of cell culture. For example, many cell culture incubators provide a humidified environment in order to prevent evaporation of cell culture media. In the context of automated cell culture systems (e.g., cell culture incubators comprising electronically-controlled mechanical components), humidified environments within incubator cabinets increase exposure of the culture to potential contaminants, including cross-contamination from growth of microorganisms (e.g., mold, biofilm-forming bacteria) on electronic equipment and insulation of electronic equipment. Furthermore, condensation resulting from a humidified environment causes rusting and malfunction of electronic equipment.

The methods and apparatus for culturing mammalian cells in a non-humidified incubator cabinet described in this document overcome these issues. This document is based, in part, on development of cell culture vessel storage compartments that comprise a gas permeable membrane that is not permeable to water vapor. In some embodiments, the described compartments create a humidified sub-environment for the culture of mammalian cells, which allows the compartments to be placed within a non-humidified incubator cabinet along with electronic components.

Selectively Permeable Cell Culture Vessel Storage Compartments

In some aspects, this document provides a container for enclosing a cell culture vessel, the container comprising: a compartment having one or more walls configured to enclose a cell culture vessel within an interior, wherein a portion of at least one wall of the compartment comprises a gas permeable membrane that is selectively impermeable to water vapor.

As used herein, "gas permeable" refers to the ability of a membrane to allow exchange of one or more gases, such as $O_2$, $CO_2$, $N_2$, and air from one side of the barrier to the other. The rate at which a permeable membrane permits the passage of gas can vary depending upon factors such as environmental conditions (e.g., temperature, pressure) and the type of gas (e.g., $O_2$, $CO_2$, $N_2$) traveling through the membrane. In some embodiments, a gas permeable membrane passes a gas at a rate ranging from about 0.25 mol/m$^2$·day to about 1.5 mol/m$^2$·day at 25° C. and 1 atmosphere (1 atm). In some embodiments, a gas permeable membrane passes a gas at a rate ranging from about 0.2 mol/m$^2$·day to about 2.0 mol/m$^2$·day at 25° C. and 1 atmosphere (1 atm). In some embodiments, a gas permeable membrane passes a gas at a rate ranging greater than 2.0 mol/m$^2$·day at 25° C. and 1 atmosphere (1 atm). Movement of gas across a gas permeable membrane can be measured by any suitable method known in the art, for example measurement of cell culture pH using PH sensitive dyes. In some embodiments, a gas permeable membrane is permeable to $O_2$ and $CO_2$.

The thickness of a gas permeable membrane can vary. In some embodiments, a gas permeable membrane ranges in thickness from about 0.1 μm to about 200 μm. In some embodiments, a gas permeable membrane ranges in thickness from about 1 μm to about 100 μm. In some embodiments, a gas permeable membrane ranges in thickness from about 10 μm to about 50 μm. In some embodiments, a gas permeable membrane ranges in thickness from about 0.1 μm to about 1 μm. In some embodiments, a gas permeable membrane is about 0.1, about 0.2, about 0.3, about 0.4, about 0.5, about 0.6, about 0.7, about 0.8, about 0.9, or about 1.0 μm thick.

Without wishing to be bound by any particular theory, the surface area of a gas permeable membrane must be large enough allow the passage of gas (e.g., $O_2$, $CO_2$) in an amount sufficient (e.g., at a rate sufficient) to maintain the viability of the cells being cultured in the container. For example, if a cell culture housed in a container requires the exchange of 2.0 mol/m2·day at 25° C. and 1 atm, then the surface area of the gas permeable membrane of the container must be sufficient to allow the passage of at least 2.0 mol/m$^2$·day at 25° C. and 1 atm. In some embodiments, the surface area of a gas permeable membrane is expressed as a percentage of the surface area of the container on which it is located (e.g., the total surface area of the container). The surface area of a gas permeable membrane can range from about 0.5% to about 99.9% of the surface area of a container. In some embodiments, the surface area of a gas permeable membrane ranges from about 1% to about 10%, about 5% to about 20%, about 10% to about 40% about 20% to about 80%, or about 50% to about 99% of the surface area of a container.

In some embodiments, the surface area of a gas permeable membrane is expressed as a percentage of the surface area of the wall that physically interfaces with the membrane (e.g., one side of the container). The surface area of a gas permeable membrane can range from about 0.5% to about 99.9% of the surface area of the wall that physically interfaces with the membrane (e.g., one side of the container). In some embodiments, the surface area of a gas permeable membrane ranges from about 1% to about 10%, about 5% to about 20%, about 10% to about 40% about 20% to about 80%, or about 50% to about 99% of the surface area of the wall that physically interfaces with the membrane (e.g., one side of the container).

As used herein, a "gas permeable membrane that is selectively impermeable to water vapor" refers to a physical barrier that permits the passage of gas (e.g., $O_2$, $CO_2$, $N_2$, etc.) but does not substantially permit the passage of liquid water or water vapor. Generally, a gas permeable membrane that is selectively impermeable to water vapor is made of a polymeric material. Examples of polymeric materials include, but are not limited to, polyethylene, polytetrafluoroethylene (Teflon®), polyvinylchloride, polyvinylidine fluoride (PVDF), natural rubber, dimethylsilicon rubber, polyethersulfonate (PES), and fluorinated ethylene-propylene (FEP). In some embodiments, a gas permeable membrane that is selectively impermeable to water vapor is hydrophobic (e.g., carries a negative surface charge). Without wishing to be bound by any particular theory, hydrophobic membranes prevent the passage of aqueous solutions (e.g., liquids) but allow the passage of gases.

In some aspects, the invention relates to the recognition that cell culture vessel storage containers comprising a gas permeable membrane that is selectively impermeable to water vapor allow the culture of mammalian cells in non-humidified cell culture incubators. As used herein, a membrane that is "selectively impermeable to water vapor" means that a substantial amount of water (e.g., liquid $H_2O$) or water vapor cannot flow across the membrane (e.g., a gas permeable membrane). In some embodiments, a membrane that is selectively impermeable to water vapor passes no more than 5 mol/m$^2$·day at 25° C. and 1 atmosphere (1 atm). In some embodiments, a membrane that is selectively impermeable to water vapor passes no more than 2.5 mol/m$^2$·day at 25° C. and 1 atmosphere (1 atm). In some embodiments, a membrane that is selectively impermeable to water vapor passes no more than 0.25 mol/m$^2$·day at 25° C. and 1 atmosphere (1 atm).

As used herein, a "container" is a device configured to house a cell culture vessel. A container can have 1 wall, 2 walls, 3 walls, 4 walls, 5 walls, or 6 walls. In some embodiments a container has more than 6 walls. The walls of a container can be made of any suitable material, for example plastic (e.g., polystyrene, polycarbonate, polyethylene), glass, metal (e.g., stainless steel, aluminum), or any combination of the foregoing.

This document is based, in part, on a recognition that, in some embodiments, a container having walls made of a material characterized by a low water vapor transmission rate (WVTR) results in lower absorption of water vapor by the walls of the container and improved regulation of environmental conditions (e.g., relative humidity) inside the container relative to a container having walls characterized by high WVTR (e.g., certain types of polymers, e.g., plastics such as polystyrene). Non-limiting examples of the WVTRs of certain materials are depicted in Table 1 below.

TABLE 1

| Examples of Water Vapor Transmission Rates (WVRTs) | |
|---|---|
| Material | WVTR (g/m$^2$ day) |
| PMMA (Acrylic) | 55.2 |
| HDPE | 4.6-6.2 |
| PP (Polypropylene) | 3.9 |
| PS (Polystyrene) | 1200-6100 |
| FEP (25 μm) | 7.0 |
| Alum. Foil | <.001 |

In some embodiments, the one or more walls of the container is (are) made of a material having a low WVTR. In some embodiments, one or more walls of the container are made of metal, for example aluminum. In some embodiments, one or more walls of the container are coated with a material having a lot WVTR. For example, in some embodiments, one or more walls of the container are coated in a metal, such as aluminum.

In some embodiments, a low WVTR refers to a WVTR ranging from about 0 (e.g., completely water vapor impermeable) to about 30 g/m$^2$ day, about 0 (e.g., completely water vapor impermeable) to about 15 g/m$^2$ day, about 0 (e.g., completely water vapor impermeable) to about 10 g/m$^2$ day. In some embodiments, a low WVTR refers to a WVTR of less than 10 g/m$^2$ day, less than 9 g/m$^2$ day, less than 8 g/m$^2$ day, less than 7 g/m$^2$ day, less than 6 g/m$^2$ day, less than 5 g/m$^2$ day, less than 4 g/m$^2$ day, less than 3 g/m$^2$ day, less than 2 g/m$^2$ day, or less than 1 g/m$^2$ day, less than 0.1 g/m$^2$ day, less than 0.01 g/m$^2$ day, less than 0.001 g/m$^2$ day, or less than 0.0001 g/m$^2$ day.

In some embodiments, a high WVTR refers to a WVTR that is greater than about 30 g/m$^2$ day. In some embodiments, a high WVTR refers to a WVTR between about 31 g/m$^2$ day to about 10,000 g/m$^2$ day. In some embodiments, a high WVTR refers to a WVTR between about 50 g/m$^2$ day and about 6500 g/m$^2$ day.

A wall can have a solid, contiguous surface or may comprise passages. In some embodiments, the one or more passages are covered by a gas permeable membrane that is selectively impermeable to water (e.g., liquid or vapor). In some embodiments, each wall of a container is the same size (e.g., has identical dimensions). In some embodiments, the one or more walls of a container are not the same size (e.g., do not have identical dimensions). For example, in some embodiments a container may have a cuboidal shape.

In some embodiments, one wall of a container (e.g., a cuboidal container) forms a bottom surface of the container that is configured for holding a microplate (e.g., forms a floor of the container on which a microplate may rest). In some aspects, this document provides a container floor comprising one or more microplate retention devices configured to properly position and/or secure a microplate inside the container. For example, in some embodiments, a container floor comprises "feet" or "locators". As used herein, a "foot" (also referred to as a "locator" or "rib") is a structure attached (e.g., glued, molded, soldered, etc.) to the floor of a container that provides a surface upon which a microplate rests. In some embodiments, a foot (or locator, or rib) prevents the microplate from contacting or resting on the floor of a container. In some embodiments, a container comprises 1, 2, 3, 4, 5, 6, 7, 8, 9, 10, or more microplate retention devices.

Generally, a microplate retention device (e.g., a foot, locator, rib, etc.) may have any shape which allows prevents a microplate from contacting the container floor (e.g., prevents the microplate from sitting flat on the container floor). In some embodiments, a microplate retention device is a straight, elongated structure that runs the length or width of the container floor. (e.g., a rib). In some embodiments, a microplate retention device is formed by one or more (e.g., two, three, or four) opposing structures having 90 degree angles (e.g., an "L" shaped locator).

In some embodiments, at least one wall of a container is a configured to physically interface with a gas permeable membrane. As used herein, a "physical interface" refers to one or more points of contact that join two or more components of a container (e.g., a wall and a gas permeable membrane, two or more walls and a support structure, a door and a hinge, etc.). A physical interface can be formed or stabilized (e.g., held together) by physical means (e.g., pressure, clamping, magnetism), chemical means (e.g., covalent or non-covalent bonding), or a combination of physical and chemical means. In some embodiments, a physical interface is formed when two or more components are joined together by an adhesive, for example an epoxy, a resin, a glue, or a weld (e.g., the one or more components are fused together by heating). In some embodiments, a physical interface is gas-impermeable (e.g., airtight). A physical interface may be permanent (e.g., irreversible, such as chemical bonding) or temporary. For example, in some embodiments, a physical interface between a gas permeable membrane and a wall of a container is temporary (e.g., the membrane is removable, or readily detachable from the wall).

In some embodiments, a container comprises at least one wall that physically interfaces with a support structure. A "support structure" refers to a solid material that provides a rigid framework for a component of a container. For example, in some embodiments, a support structure is a plurality of rods that physically interface with one another to form the frame of a container; the resulting frame physically interfaces with one or more walls to form a container comprising a compartment configured to enclose a cell culture vessel within an interior. In some embodiments, a support structure is a wall. For example a wall having one or more passages (e.g., one or more holes) can physically interface with a gas permeable membrane and thus function as a support structure for the gas permeable membrane.

In some embodiments, a container as described by this document comprises one or more passages to an interior compartment. In some embodiments, container passages to an interior compartment can be of any size, e.g., any size suitable for passing items into and out from the container. For example, in some embodiments, a container passage can be suitable for passing a conduit or tube into the container or large enough to pass a cell culture vessel through. A container passage can be of any suitable shape, including, for example, circular, elliptical, polygonal, rectangular, etc. In some embodiments, a container passage may have a diameter, diagonal, or other cross-sectional dimension in a range of about 500 µm to about 5 mm, about 750 µm to about 3 mm, about 1 mm to about 2 mm, about 2 cm to about 15 cm, or about 10 cm to about 25 cm. In some embodiments, a container passage may have a cross-sectional area in a range of 0.25 mm$^2$ to 25 mm$^2$, 0.5 mm$^2$ to 9 mm$^2$, 1 mm$^2$ to 4 mm$^2$, 4 cm$^2$ to 250 cm$^2$, 100 cm$^2$ to 600 cm$^2$, 0.25 mm$^2$ to 5 cm$^2$, 5 mm$^2$ to 15 cm$^2$, 5 mm$^2$ to 25 cm$^2$, or 0.25 mm$^2$ to 600 cm$^2$.

In some embodiments, a container described by this document further comprises a moveable structure configured for opening and closing a container passage. For example, a container may comprise a door that covers one passage of the container. In some embodiments, a moveable structure (e.g., a door) comprises a seal configured to interface with a surface of the container that surrounds the passage. The seal can made of any suitable material, for example grease and/or mechanical elements such as o-rings, gaskets, septa, KF, LF, QF, quick coupling, or other sealing mechanisms. In some embodiments, the seal is gas and liquid impermeable. In some embodiments, a moveable structure (e.g., a door) comprises a hinge connected (e.g., that physically interfaces with) to the compartment and configured to permit the moveable structure to rotate between an open position to a closed position. In some embodiments, a moveable structure is configured to automatically transition between an open position to a closed position in response to an input signal from a remote control unit.

In some embodiments, a moveable structure (e.g., door) is optically transparent. In some embodiments, each of the one or more walls are optically transparent. Without wishing to be bound by any particular theory, the use of optically transparent materials for movable structures and/or walls allows cells being cultured in a vessel within the container to be monitored, observed, or imaged without removing the culture from the container. For example, pH of a cell culture may be monitored by observing the color of a pH sensitive culture media through an optically transparent wall or door of a compartment. In another example, optically transparent walls or doors allow a cell culture to be imaged by microscopy (e.g., phase contrast microscopy, fluorescence microscopy) without removing the culture from the container.

In some embodiments, a container described by this document further comprises at least one exterior portion configured to interface with a second container. For example a container may contain one or more tabs or slots, such as a tongue and groove system, that allows two containers to be physically joined (e.g., connected) in a modular fashion. Physical interfaces between containers can be permanent or temporary. In some embodiments, a plurality of containers described by this document are physically connected in a modular fashion, and referred to as a "rack" of containers. In some embodiments, a plurality of containers comprises between 2 and 100 containers. In some embodiments, a plurality of containers comprises between 10 and 75 containers. In some embodiments, a plurality of containers comprises between about 15 and 25 containers. In some embodiments, a plurality of containers comprises between about 5 and 50 containers. In some embodiments a plurality of containers comprises more than 100 containers.

Cell Culture Vessels

As used herein, a "cell culture vessel" is a device including a housing and one or more chambers for culturing cells.

In some embodiments, the housing is a frame. The frame may be coupled to a lid. The one or more chambers may include cell culturing media including one or more membranes. In some embodiments, a cell culture vessel may include nutrients for promoting the growth of cells. In certain embodiments, a cell culture vessel may entirely enclose one or more cells or groups thereof. The housing of a cell culture vessel may include one or more passages to permit the transfer of gases between a cell culture vessel and its surrounding environment. In certain embodiments, a cell culture vessel includes a transparent or optically clear window. For example, a lid coupled to the housing of a cell culture vessel may include an optically clear portion for viewing cells e.g., with a microscope or other imager.

Various types of cell culture vessels can be used with the containers described herein. Cell culture vessels can be made from any non-reactive biocompatible material, such as glass, plastic or silicone. Generally, cell culture vessels are formed into bottles, flasks, vials, bags, tubes or culture plates. In some embodiments, the cell culture vessel is a vial. In some embodiments, the cell culture vessel is a bottle or flask. In some embodiments, the cell culture vessel is a culture plate. In some embodiments, the plate is a cell culture dish. In some embodiments, the plate is a multi-well culture plate. Generally multi-well plates include an array of 96, 384 or 1536 wells. In some embodiments, a cell culture vessel includes one or more portions that are substantially non-reflective. In some embodiments, the cell culture vessel is barcoded. In some embodiments, an incubator includes a barcode reader.

Cell Culture Methods

In one aspect, this document provides a method for culturing cells, the method comprising: culturing cells in a within a cell culture vessel, wherein the cell culture vessel is present within a container, the container comprising a compartment having one or more walls configured to enclose the cell culture vessel within a compartment interior, wherein a portion of at least one wall of the compartment comprises a gas permeable membrane that is selectively impermeable to water vapor. In some embodiments, the container is present within a cell culture incubator. In some embodiments, the cell culture incubator is a non-humidified cell culture incubator.

As used herein, "cell culture" refers to a procedure for maintaining and/or growing cells under controlled conditions (e.g., ex vivo). In some embodiments, cells are cultured under conditions to promote cell growth and replication, conditions to promote expression of a recombinant product, conditions to promote differentiation (e.g., into one or more tissue specific cell types), or a combination of two or more thereof.

As used herein, the term "mammalian cell sample" refers to any cell obtained from a mammalian subject. Non-limiting examples of mammalian subjects include humans, non-human primates, mice, rats, horses, dogs, cats, and guinea pigs. In some embodiments, the mammalian cell sample is obtained from a human.

In some embodiments, a cell sample is isolated from a tissue or organ (e.g., a human tissue or organ), including but not limited to solid tissues and organs. In some embodiments, cell samples can be isolated from placenta, umbilical cord, bone marrow, liver, blood, including cord blood, or any other suitable tissue. In some embodiments, patient-specific cell samples are isolated from a patient for culture (e.g., for cell expansion and optionally differentiation) and subsequent re-implantation into the same patient or into a different patient. In some embodiments, cells grown in an incubators described herein may be used for allogenic or autogeneic therapy. In some embodiments, cells grown in the incubators disclosed herein may be genetically modified, expanded and reintroduced into a patient for the purpose of providing an immunotherapy (e.g., chimeric antigen receptor therapy (CAR-T), or delivery of CRISPR/Cas modified cells).

In some embodiments, cells are isolated from tissues or biological samples for ex vivo culture in an incubator described herein. In some embodiments, cells (e.g., white blood cells) are isolated from blood. In some embodiments, cells are released from tissues or biological samples using physical and/or enzymatic disruption. In some embodiments, one or more enzymes such as collagenase, trypsin, or pronase are used to digest the extracellular matrix. In some embodiments, tissue or biological samples are placed in culture medium (e.g., with or without physical or enzymatic disruption), and cells that are released and that grow in the culture medium can be isolated for further culture.

The methods described herein are suitable for culturing a variety of mammalian cell types. In some embodiments, the mammalian cell sample is a cell useful for autologous cell therapy. As used herein, the term "autologous cell therapy" refers to the implantation, transplantation, infusion, or transfer of cultured cells back into the individual from whom the cells were obtained. For example, immune cells may be obtained from a subject having cancer, expanded into a cell culture, primed with an antigen against the cancer, and reintroduced into the patient in order to boost the subject's immune response. Examples of cells that are useful for autologous culture include but are not limited to, stem cells (e.g., hematopoietic stem cells, somatic stem cells, totipotent stem cells, pluripotent stem cells, fetal stem cells, embryonic stem cells, mesenchymal stem cells, and induced pluripotent stem cells), progenitor cells (e.g., satellite cells, neural progenitor cells, bone marrow stromal cells, pancreatic progenitor cells, angioblasts and endothelial progenitor cells), immune cells (e.g., T-lymphocytes, dendritic cells) and differentiated cells (epithelial cells, cardiomyocytes, fibroblasts, and chondrocytes).

In some embodiments, containers described herein provide an aseptic environment for the growth of cell cultures. As used herein, the term "aseptic environment" refers to the an environment lacking contaminants. For example, it may be desirable that a cell culture is imaged in an aseptic environment because non-aseptic imaging of the culture could introduce pathogens or other contaminants into the cell culture. Contaminants include but are not limited to bacteria (e.g., pathogenic bacteria and non-pathogenic bacteria), viruses (e.g., pathogenic viruses and non-pathogenic viruses), molds, spores, and dust. In some embodiments, a contaminant is a cell. For example, when cells obtained from different subjects are simultaneously cultured, aseptic transfer of materials is required so that cross-contamination (i.e., the introduction of a cell or media from one culture to a different culture) does not occur.

Aseptic techniques can be used to prevent or minimize contamination of cell cultures during growth and manipulation. In some embodiments equipment (e.g., pipettes, fluid handling devices, manipulating devices, other automated or robotic devices, etc.) that is used for cell culture is sterilized using an appropriate technique. Non-limiting techniques include heat exposure (e.g., autoclaving), surface disinfection (e.g., using alcohol, bleach, or other disinfectant), irradiation, and/or exposure to a disinfectant gas (e.g., ozone, hydrogen peroxide, etc.) as described herein. In some embodiments, media is sterilized using an appropriate technique. Non-limiting techniques include heat exposure (e.g., autoclaving), antimicrobial/antiviral treatment, filtration, and/or irradiation.

In some embodiments, manipulations of cell cultures are performed under aseptic conditions, for example, in an environment (e.g., within an incubator chamber) that has been disinfected and in which the air has been filtered to remove potential contaminants.

In some embodiments, cell cultures are grown and maintained under GMP-compliant conditions, including those that include using GMP-compliant media or GMP-compliant liquid handling equipment. In some cases, cell cultures are grown and maintained by performing methods in conjunction with standard operation procedures (SOPs).

In some aspect, this document relates to cell culture vessel containers comprising a wall or door that is optically transparent. Optically transparency of one or more sides of the containers described herein allows the cell culture inside the container to be monitored or observed aseptically. In some embodiments, cell cultures can be monitored and/or evaluated to detect contamination. In some embodiments, contamination by cells from a different type of organism can be detected. In some embodiments, contamination of a mammalian cell culture by *mycoplasma*, bacteria, yeast, or viruses can be detected using any suitable technique. In some embodiments, cell culture contamination can be detected by assaying for changes or for rates of change of one or more culture properties such as pH, turbidity, etc., that are characteristic of contamination (e.g., by bacteria or yeast) and not characteristic of the cells (e.g., mammalian cells) being grown in culture. In some embodiments, one or more molecular detection assays (e.g., PCR, ELISA, RNA labeling, or other enzymatic techniques) or cell-based assays can be used to detect contamination (e.g., *mycoplasma*, bacterial, yeast, viral, or other contamination).

In some embodiments, cell cultures can be monitored and/or evaluated to detect contamination with cells of similar types (e.g., a human cell line contaminated by different human cells or by different mammalian cells). In some embodiments, cell cultures and their potential contamination can be evaluated using DNA sequencing or DNA fingerprinting (e.g., short tandem repeat-STR-fingerprinting), isoenzyme analysis, human lymphocyte antigen (HLA) typing, chromosomal analysis, karyotyping, cell morphology, or other techniques.

In some embodiments, cells produced using the containers or methods described herein can be frozen to preserve them for later use and/or for transport. In some embodiments, cells are mixed with a cryopreservation composition after growth and/or differentiation and prior to freezing. A cryopreservation composition can be added to a cell culture vessel, or cells can be transferred from a cell culture vessel to a cryopreservation vessel along with a cryopreservation composition. Non-limiting examples of cryoprotectants that can be included in a cryopreservation composition include DMSO, glycerol, PEG, sucrose, trehalose, and dextrose. In some embodiments, a freezer may be provided as a component of an incubator to facilitate freezing of cells isolated from cell cultures. For example, one or more freezers may be located in an internal chamber and/or integrated into the incubator cabinet (e.g., into a wall of the incubator cabinet).

In some embodiments, cell culture vessels may be pre-kitted with one or more reagents desired for a particular purpose, e.g., for growing cells, for differentiating cells, for subjecting cells to a particular assay condition, etc. In some embodiments, pre-kitted cell culture vessels contain reagents useful for performing a particular experiment (e.g., cell growth media, growth factors, selection agents, labeling agents, etc.) on a cell culture, in advance of the experiment. Pre-kitted cell culture vessels may facilitate experimental protocols by providing cell culture-ready vessels that do not require the addition of reagents. For example, progenitor cells from a patient may be added to a cell culture vessel pre-kitted with reagents for cell differentiation for the purpose of expanding a population of differentiated cells for autologous cell therapy. Pre-kitted cell culture vessels can be stored at any appropriate temperature, which is determined by the recommended storage parameters of the reagents within the pre-kitted cell culture vessel. In some embodiments, pre-kitted cell culture storage vessels are stored prior to use at temperatures between about $-80°$ C. and about $37°$ C. In some embodiments, pre-kitted cell culture storage vessels are stored prior to use at temperatures between about $-80°$ C. and about $-20°$ C. In some embodiments, pre-kitted cell culture storage vessels are stored prior to use at temperatures between about $-20°$ C. and about $4°$ C. In some embodiments, pre-kitted cell culture storage vessels are stored prior to use at temperatures between about $4°$ C. and about $37°$ C. In some embodiments, pre-kitted cell culture vessels are disposable. In some embodiments, pre-kitted cell culture vessels are reusable and/or refillable.

In some embodiments, cell culture vessels are configured for culturing cells in suspension. In some embodiments, cell culture vessels are configured for culturing adherent cells. In some embodiments, cell culture vessels are configured for 2D or 3D cell culture. In some embodiments, cell culture vessels include one or more surfaces or micro-carriers to support cell growth. In some embodiments, these are coated with extracellular matrix components (e.g., collagen, fibrin and/or laminin components) to increase adhesion properties and/or to provide other signals needed for growth and differentiation. In some embodiments, cell culture vessels include one or more synthetic hydrogels such as polyacrylamide or polyethylene glycol (PEG) gels to support cell growth. In some embodiments, cell culture vessels include a solid support with embedded nutrients (e.g., a gel or agar, for example for certain bacterial or yeast cultures). In some embodiments, cell culture vessels include a liquid culture medium.

In some embodiments, growth media is aseptically introduced into the cell culture vessel. As used herein, the term "growth media" refers to a medium for culturing cells containing nutrients that maintain cell viability and support proliferation. In some cases various parameters and conditions can be used for culturing cells. The growth media may contain any of the following nutrients in appropriate amounts and combination: salt(s), buffer(s), amino acids, glucose or other sugar(s), antibiotics, serum or serum replacement, and other components such as peptide growth factors, etc. Growth media are known in the art and may be classified as natural or artificial media. Examples of cell culture media include but are not limited to Minimum Essential Medium (MEM), Dulbecco's Modified Eagle's Medium (DMEM), and Roswell Park Memorial Institute Medium (RPMI). An appropriate medium for culturing the cell may be selected.

In some embodiments, cells are cultured in one of any suitable culture media. Different culture media having different ranges of pH, glucose concentration, growth factors, and other supplements can be used for different cell types or for different applications. In some embodiments, custom cell culture media or commercially available cell culture media such as Dulbecco's Modified Eagle Medium, Minimum Essential Medium, RPMI medium, HA or HAT medium, or other media available from Life Technologies or other commercial sources can be used. In some embodiments, cell culture media include serum (e.g., fetal bovine serum, bovine calf serum, equine serum, porcine serum, or other serum). In some embodiments, cell culture media are serum-free. In some embodiments, cell culture media include human platelet lysate (hPL). In some embodiments, cell culture media include one or more antibiotics (e.g., actinomycin D, ampicillin, carbenicillin, cefotaxime, fosmidomycin, gentamycin, kanamycin, neomycin, penicillin, penicillin streptomycin, polymyxin B, streptomycin, tetracycline, or any other suitable antibiotic or any combination of two or more thereof). In some embodiments, cell culture media include one or more salts (e.g., balanced salts, calcium chloride, sodium chloride, potassium chloride, magnesium chloride, etc.). In some embodiments, cell culture media include sodium bicarbonate. In some embodiments, cell culture media include one or more buffers (e.g., HEPES or other suitable buffer). In some embodiments, one or more supplements are included. Non-limiting examples of supplements include reducing agents (e.g., 2-mercaptoethanol), amino acids, cholesterol supplements, vitamins, transferrin, surfactants (e.g., non-ionic surfactants), CHO supplements, primary cell supplements, yeast solutions, or any combination of two or more thereof. In some embodiments, one or more growth or differentiation factors are added to cell culture media. Growth or differentiation factors (e.g., WNT-family proteins, BMP-family proteins, IGF-family proteins, etc.) can be added individually or in combination, e.g., as a differentiation cocktail including different factors that bring about differentiation toward a particular lineage. Growth or differentiation factors and other aspects of a liquid media can be added using automated liquid handlers integrated as part of an incubator provided herein.

In some embodiments, biological material is aseptically introduced into the cell culture vessel. Examples of biological materials include but are not limited to growth factors, nucleic acids, and expression vectors. Growth factors are naturally occurring substances that stimulate cell growth, proliferation, healing and/or differentiation. Generally, growth factors are proteins or steroid hormones. In the context of mammalian cell culture, growth factors may be introduced to culture media in order to control the cell cycle or induce proliferation or differentiation of cultured cells. Non-limiting examples of growth factors include angiopoietin, bone morphogenic proteins (BMPs), epidermal growth factor (EGF), brain-derived neurotrophic factor (BDNF), erythropoietin (EPO), fibroblast growth factor (FGF), granulocyte colony-stimulating factor (G-CSF), insulin-like growth factor (IGF), nerve growth factor (NGF), transforming growth factor beta (TGF-β), and vascular endothelial growth factor (VEGF).

In some embodiments, the biological material is a nucleic acid or expression vector. For example, somatic cells can be "reprogrammed" to become induced stem cells via the introduction of genetic material encoding reprogramming protein factors and microRNA. In some embodiments, the methods provided herein further included aseptic introduction of a nucleic acid or expression vector into the cell culture vessel. In some embodiments, a nucleic acid is introduced to the cell culture. Examples of nucleic acids include DNA, RNA, siRNA, miRNA, ami-RNA, shRNA, and dsRNA. In some embodiments, an expression vector is introduced into the cell culture vessel. The term "expression vector" refers to an engineered molecule capable of artificially carrying foreign genetic material into another cell and expressing the genetic material in the cell. Expression vectors can generally be classified as transfection vectors and transduction vectors. Transfection vectors (e.g., DNA-based plasmid vectors) are generally used for non-virally-mediated transfer of genetic material into cells. Transduction vectors (e.g., lentivital vectors, AAV vectors, rAAV vectors, and retroviral vectors) are generally used for virally-mediated transfer of genetic material into cells. In some embodiments, the expression vector includes a transgene. The composition of the transgene sequence of an expression vector will depend upon the use to which the resulting vector will be put. For example, one type of transgene sequence includes a reporter sequence, which upon expression produces a detectable signal. In another example, the transgene encodes a therapeutic protein or therapeutic functional RNA.

In some aspects, this documents relates to methods for monitoring cells under controlled conditions (e.g., under aseptic and/or sterile conditions). In some aspects, methods described herein are useful for cell culture (e.g., to grow and maintain cells for recombinant protein expression or to grow and/or differentiate cells for therapeutic applications such as implantation). In some embodiments, the conditions (e.g., environment) inside incubators provided herein are monitored. In some cases, the temperature, humidity, carbon dioxide, oxygen and other gaseous components inside the incubator may be monitored. In some embodiments, the conditions (e.g., temperature, oxygen, carbon dioxide, and pH) of the growth media are monitored. Growth media conditions can be monitored directly, via probes and sensors, or indirectly via colorimetric (e.g., media containing Phenol Red) or imaging techniques (e.g., infrared or thermal imaging). In some embodiments, conditions of growth media and cells are monitored by aseptically removing an aliquot contains growth media and cells from a culture vessel and analyzing the aliquot at a location external to the culture vessel. In some embodiments, the aliquot is filtered, for example, by centrifugation to separate the cells from the growth media.

In some embodiments, containers and methods described herein are used to monitor or assay culture media for nutrient depletion, changes in pH, changes in temperature, accumulation of apoptotic or necrotic cells, and/or cell density. In some embodiments, containers and methods described herein are used to modify or change the culture media or conditions and/or to passage the cell cultures when appropriate. In some embodiments, the methods described herein are automated.

Cell Culture Systems

In some aspects, this document relates to cell culture systems including an incubator cabinet. In some embodiments, an incubator cabinet as described herein is a non-humidified incubator cabinet. Without wishing to be bound by any particular theory, cell culture vessel containers described herein provide a humidified sub-environment for the culture of mammalian cells in a non-humidified incubator. As used herein, "non-humidified incubator cabinet" refers to an incubator cabinet lacking a humidifying source (e.g., an open water source, humidifier, etc.). In some embodiments, a non-humidified incubator cabinet comprises one or more electronic devices.

As used herein, an "incubator cabinet" is a housing that includes one or more chambers configured to hold one or more cell culture vessels. In some embodiments, an incubator cabinet is configured to hold one or more containers as described herein. In some embodiments, an incubator cabinet is configured to hold a rack of containers as described herein. In some embodiments, an incubator cabinet is configured to hold more than one rack of containers as described herein.

In some embodiments, an incubator cabinet (e.g., a non-humidified incubator cabinet) includes a transfer chamber and an internal chamber, one or both of which are configured to hold one or more containers. In some embodiments, an incubator may include one or more other elements such as one or more gas sources (e.g., a gas cylinder or ozone generator), tubing (e.g., to convey one or more liquids or gases such as water, distilled water, deionized water, cell culture medium, air, carbon dioxide, ozone, and oxygen), airflow mechanisms (e.g., valves, release valves, pinholes, gas regulators, and mass flow regulators), pressure mechanisms (e.g., a pump such as a dry scroll pump, rotary pump, momentum transfer pump, diffusion pump, or diaphragm pump; a suction tube; a vacuum system; and an air blower), environmental monitors and controls (e.g., a gas sensor and/or monitor to sense and/or control concentrations of gases such as carbon dioxide, oxygen, and ozone; heat sources or sinks; temperature monitors and controls; humidity monitors; gas scrubbers; air filters; instrumentation for measuring particulate matter; pressure gauges; and flow meters), doors (e.g., panels), windows (e.g., optical windows made of glass, plastic, composite, or other substantially transparent material for viewing an area inside the incubator cabinet), ports (e.g., to permit the introduction or removal of one or more gases or liquids), light sources (e.g., lamps, bulbs, lasers, and diodes), optical elements (e.g., microscope objectives, mirrors, lenses, filters, apertures, wave plates, windows, polarizers, fibers, beam splitters, and beam combiners), imaging elements (e.g., cameras, barcode readers), electrical elements (e.g., circuits, cables, power cords, and power supplies such as batteries, generators, and direct or alternating current supplies), computers, mechanical elements (e.g., motors, wheels, gears, robotic elements, and actuators such as pneumatic actuators, electromagnetic actuators, motors with cams, piezoelectric actuators, and motors with lead screws), and control elements (e.g., spin-wheels, buttons, keys, toggles, switches, cursors, screws, dials, screens, and touch-screens). In some embodiments, one or more of these other elements are part of the incubator, but are external to the incubator cabinet. In some embodiments, one or more of these other elements are included within the incubator cabinet.

In some embodiments this document relates to incubators (e.g., non-humidified incubators) comprising cell culture containers and methods for culturing, manipulating, and/or monitoring cells under controlled conditions (e.g., under aseptic and/or sterile conditions). In some embodiments, the cell culture incubators include an incubator cabinet having an internal chamber for incubation of cells in one or more cell culture vessels, wherein each of the one or more cell culture vessels is housed in a container as described herein. In some cases, in addition to an internal door from the transfer chamber to the internal chamber, the incubators include at least one external door (e.g., 1, 2, 3, 4, or more external doors) opening from an external environment directly to the internal chamber, for example, to provide alternative access to the internal chamber during periods of time when the incubator is not operational, e.g., during maintenance of the incubator. In some embodiments, incubators include a storage location within the internal chamber for storing one or more cell culture vessels.

In some embodiments, incubators or incubator cabinets (e.g., non-humidified incubators or incubator cabinets) provided herein are rectangularly cuboidal in shape. In some embodiments incubators or incubator cabinets provided herein have a rectangular footprint in a range of 1 $ft^2$ to 16 $ft^2$. In some embodiments incubators or incubator cabinets provided herein have a rectangular footprint of up to about 1 $ft^2$, 2 $ft^2$, 3 $ft^2$, 4 $ft^2$, 5 $ft^2$, 6 $ft^2$, 7 $ft^2$, 8 $ft^2$, 9 $ft^2$, 10 $ft^2$, 11 $ft^2$, 12 $ft^2$, 13 $ft^2$, 14 $ft^2$, 15 $ft^2$, or 16 $ft^2$. In some embodiments incubators or incubator cabinets provided herein have a total chamber volume in a range of 1 $ft^3$ to 100 $ft^3$. In some embodiments incubators or incubator cabinets provided herein have a chamber volume of up to about 1 $ft^3$, 5 $ft^3$, 10 $ft^3$, 25 $ft^3$, 50 $ft^3$ or 100 $ft^3$. In some embodiments incubators or incubator cabinets provided herein have a rectangular footprint in a range of 0.09 $m^2$ to 1.78 $m^2$. In some embodiments incubators or incubator cabinets provided herein have a rectangular footprint of up to about 0.1 $m^2$, 0.2 $m^2$, 0.3 $m^2$, 0.4 $m^2$, 0.5 $m^2$, 0.6 $m^2$, 0.7 $m^2$, 0.8 $m^2$, 0.9 $m^2$, 1.0 $m^2$, 1.1 $m^2$, 1.2 $m^2$, 1.3 $m^2$, 1.4 $m^2$, 1.5 $m^2$, 1.6 $m^2$, or 1.7 $m^2$. In some embodiments, incubators or incubator cabinets provided herein have a total chamber volume in a range of 0.03 $m^3$ to 3 $m^3$. In some embodiments incubators or incubator cabinets provided herein have a chamber volume of up to about 0.03 $m^3$, 0.1 $m^3$, 0.3 $m^3$, 1 $m^3$, or 3 $m^3$.

In some embodiments, an incubator cabinet is single-walled. In some embodiments, an incubator is double-walled. In some embodiments, insulation material is provided between the double walls of an incubator cabinet to control heat loss from the cabinet and facilitate temperature control in the cabinet. In some embodiments, the outer wall of an incubator cabinet includes a sheet metal, e.g., a 14-20 gauge cold rolled steel. In some embodiments, an inner wall (e.g., a chamber surface) of an incubator cabinet includes electro-polished stainless steel. In some embodiments, an inner wall (e.g., a chamber surface) of an incubator cabinet includes corrosion resistant materials, such as, titanium, cobalt-chrome, tantalum, platinum, zirconium, niobium, stainless steel, and alloys thereof. However, in some embodiments, a chamber surface of an incubator cabinet includes a polymeric material such as polytetrafluoroethylene (PTFE), or a polymeric material know under the trade name of Parylene. In some embodiments, a chamber surface may have anti-microbial properties, such as copper or silver or anti-microbial compounds incorporated into a polymeric surface coating.

In some embodiments, the incubator (e.g., a non-humidified incubator) includes an airlock arrangement that may be used to help decreases exposure of the internal chamber to the external environment, or exposure of the external environment to the internal chamber. For example, an incubator cabinet may include an external door leading to a transfer chamber and an internal chamber, wherein the transfer chamber and the internal chamber are physically separated by a wall having an internal door. In some embodiments, to utilize the airlock arrangement, one door is opened at a time. For example, an operator may open the external door to gain access to the transfer chamber. The operator may then insert item(s) such as pipette tips into the transfer chamber. An operator may operate the external door by directly manipulating the door. In some embodiments, an operator may operate the door indirectly by controlling the operation of the door remotely, e.g., through the use of automation configured to control opening and closing of the doors. In some embodiments, the internal chamber door remains closed while the external door is open. In some embodiments, after item(s) are inserted into the transfer chamber, the external door is closed (e.g., directly or indirectly by an operator). Once the external door is closed, a sterilization process inside the transfer chamber is used to sterilize the inserted item(s). Once sterilization is complete, the internal chamber door is opened, and the sterilized items are moved from the transfer chamber into the internal chamber (e.g., by one or more transfer devices).

In some embodiments, the transfer chamber and/or the internal chamber may have a gas-tight or hermetic seal, e.g., around one or more windows or doors. In particular embodiments, sealants such as grease and/or mechanical elements such as o-rings, gaskets, septa, KF, LF, QF, quick coupling, or other sealing mechanisms may be used to establish one or more gas-tight seals. In some embodiments, grooves, depressions, protrusions, and/or molded plastic elements may facilitate in establishing one or more gas-tight seals. In some embodiments, an incubator (e.g., an internal chamber, and/or a transfer chamber of an incubator cabinet) includes one or more windows and/or doors, that, when closed, are sealed to preserve sterility (e.g., after one or more chambers of the incubator have been sterilized). In some embodiments, each seal of the incubator is air tight up to a threshold level of pressure (e.g., up to 1 atm). In some embodiments, a gasket is provided to ensure a desired level of sealing capacity. In general, a "gasket" is understood as a mechanical seal that fills the space between two objects, generally to prevent leakage between the two objects while under compression. Gaskets are commonly produced by cutting from sheet materials, such as gasket paper, rubber, silicone, metal, cork, felt, neoprene, nitrile rubber, fiberglass, or a plastic polymer (such as polychlorotrifluoro-ethylene). It is often desirable that a gasket be made from a material that provides some degree of yielding such that it is able to deform and fill tightly the space it is designed for, including any slight irregularities. In some embodiments, gaskets can be used with an application of sealant directly to the gasket surface to function properly. In some embodiments, a gasket material can be a closed-cell neoprene foam which is non-reactive with carbon dioxide or ozone.

Internal Chambers

As used herein, an "internal chamber" is a chamber disposed in an incubator cabinet (e.g., a non-humidified incubator cabinet). An internal chamber may include one or more windows (e.g., optical windows made of glass, plastic, composite, or other substantially transparent material for viewing an area inside the incubator cabinet). An internal chamber may include at least one door (e.g., for permitting the transfer of items into or out of the internal chamber). In some embodiments, the at least one door may be disposed between the internal chamber and a transfer chamber. In certain embodiments, an interlock may prevent the door from opening at an undesirable time (e.g., when a portion of the incubator cabinet is open to the surrounding environment so that contaminants cannot enter the internal chamber). An internal chamber may be of any appropriate size and geometry. In some embodiments, an incubator cabinet may include more than one internal chamber. In other embodiments, an internal chamber may include one or more partitions to define different regions of an internal chamber. One or more internal chambers or partitions thereof may have different environmental conditions. The environment (e.g., air pressure, gas content, temperature, light, and humidity) inside an internal chamber may be measured and/or controlled by one or more meters, monitors, sensors, controls, pumps, valves, apertures, and/or light sources. In some embodiments, an internal chamber may have a gas-tight or hermetic seal, e.g., around one or more windows or doors. In particular embodiments, sealants such as grease and/or mechanical elements such as o-rings, gaskets, septa, KF, LF, QF, quick coupling, or other sealing mechanisms may be used to establish one or more gas-tight seals. In some embodiments, grooves, depressions, protrusions, and/or molded plastic elements may facilitate in establishing one or more gas-tight seals.

An internal chamber may be made of any useful material. In some embodiments, an internal chamber may include one or more plastics, polymers, metals, or glasses.

As used herein, a "door" is an element that permits communication between two or more environments or regions when opened and prevents communication between the two or more environments or regions when closed. A door may be of any type, such as a sliding door, pocket door, swinging door, hinged door, revolving door, pivot door, or folding door. The door may be manually, mechanically, or electrically operated. For example, an operator may open or close a door by manually grasping, pulling, pushing, and/or otherwise physically interacting with the door or an element thereof (e.g., a handle) or by operating a mechanical control (e.g., a button, toggle, spin-wheel, key, switch, cursor, screw, dial, screen, or touch-screen). In certain embodiments, a door may be controlled by electrical or digital controls, such as by a computer. A door may be an automatically opening door. For example, a door may include a sensor, such as a pressure, infrared, motion, or remote sensor that detects whether the door is open or closed and/or controls when the door opens or closes. A door may open by mechanical, pneumatic, electrical, or other means. In some embodiments, one or more doors may include one or more locking mechanisms. In particular environments, one or more doors may include one or more interlocks (e.g., a mechanical interlock such as a pin, bar, or lock or an electrical interlock such as a switch) to prevent one or more doors from opening at an undesirable time (e.g., when one or more chambers are open to the outside environment).

A transfer device for moving one or more items may be used to move items between the transfer chamber and the internal chamber. In some embodiments, the transfer device includes a conveyor belt or other similar device for maneuvering items. Non-limiting examples of items that can be moved by transfer devices include cell culture vessel containers (e.g., racks of cell culture vessel containers), cell culture vessels, pipettes, containers, syringes, and other materials and instruments utilized in the culture of cells. In some embodiments, more than one transfer device may be included. In some embodiments, one or more transfer devices are located in the transfer chamber and/or in the internal chamber. In some embodiments, a transfer device may include one or more robotic elements. For example, a transfer device may include one or more robotic arms capable of gripping, lifting, pushing, grabbing, sliding, rotating, translating, releasing, raising, lowering, and/or tilting one or more items (e.g., pipettes).

In some embodiments, the transfer device is a cell culture vessel container transfer device. As used herein, a "cell culture vessel container transfer device" refers to a device that can transfer one or more cell culture vessel containers from a first location to a second location. In some embodiments, the transfer device is anchored within the internal chamber. In certain embodiments, the transfer device may transfer one or more items to or from multiple locations in an incubator cabinet. For example, a cell culture vessel container transfer device may be used to move a cell culture vessel container from a transfer chamber to an internal chamber, and/or from a storage location (e.g., a rack of cell culture vessel containers) to an imaging location. In some embodiments, an incubator cabinet includes more than one transfer device, for moving one or more items (e.g., separate transfer devices for transferring items between and within chambers). A cell culture vessel container transfer device may include one or more elements such as valves (e.g., electromagnetic or pneumatic valves), gears, motors (e.g., electrical or stepper motors), stages (e.g., xy or xyz stages), pistons, brakes, cables, ball-screw assemblies, rack-and-pinion arrangements, grippers, arms, pivot points, joints, translational elements, or other mechanical or electrical elements. In some embodiments, a cell culture vessel container transfer device may include one or more robotic elements. For example, a cell culture vessel container transfer device may include a robotic arm capable of gripping, lifting, pushing, grabbing, sliding, rotating, translating, releasing, raising, lowering, and/or tilting one or more cell culture vessels. In preferred embodiments, the cell culture vessel container transfer device selectively and releasably grips one or more cell culture vessel containers. In certain embodiments, a cell culture vessel container transfer device may include an arm coupled to a mechanical gripper. For example, an arm may include a mechanical gripper at or near one end for releasably gripping a cell culture vessel container and be securely coupled to a surface or element of the incubator at or near the other end. In some embodiments, a robotic arm includes a pivot point where the mechanical gripper couples to the arm and one or more pivot and/or translational joints along the arm to permit flexible rotation and translation of a portion of the arm. In this manner, a robotic arm may access one or more cell culture vessel containers at different horizontal and vertical positions within an incubator cabinet (e.g., within a storage array in an internal chamber).

In some aspects, this document provides a cell culture container transfer device comprising a crank-slider mechanism that travels in a linear manner attached to two horizontally opposed, parallel arms, each arm comprising one or more grippers. In some embodiments, the crank-slider mechanism travels along a single rail. In some embodiments, the crank-slider mechanism travels along two (e.g., two parallel) rails. In some embodiments, the one or more grippers are configured to contact (e.g., hold, secure and/or pick up) a microplate. For example, in some embodiments, each gripper of a cell culture container transfer device comprises one or more surfaces (e.g. pads) for securely contacting a cell culture container (e.g., a microplate). The surface configured for contacting a microplate can be rubber, metal (e.g., magnetic), or plastic. In some embodiments, the cell culture container transfer device is configured for transferring a cell culture container into or out of a selectively permeable cell culture vessel storage container as described by this document.

In some aspects, the disclosure provides a device for moving a multi-well culture plate, the device comprising: a support structure; a motor attached to the support structure, the motor comprising a rotor, a plate holder configured to translate along a longitudinal axis of a guide rail of the support structure, the plate holder comprises two, opposed arms extending parallel to the longitudinal axis of the guide rail, wherein each arm comprises one or more contact surfaces for engaging with the multi-well culture plate; a manipulator arm comprising a proximal region coupled to the rotor, a distal region coupled to the plate holder and an elbow positioned between the proximal region and distal region, wherein the manipulator arm is configured to convert torque imparted through the rotor to a translational force imparted on the plate holder to cause the plate holder to translate along longitudinal axis of a guide rail.

In some embodiments, a cell culture vessel container transfer device is an automated transfer device. For example, the automated transfer device may be a robotic arm controlled by a computer that is programmed to move cell culture vessel containers from a storage location within the internal chamber of the incubator to an imaging location within the internal chamber of the incubator. In some embodiments, a cell culture vessel container transfer device is manually operated. For example, a robotic arm located inside the internal chamber of an incubator may be operated by a user-controlled joystick from a location outside of the internal chamber of the incubator in order to move cell culture vessel containers from a storage location (e.g., a rack of cell culture vessel containers) within the internal chamber of the incubator to an imaging location within the internal chamber of the incubator.

As used herein, a "storage location" refers to a location at which one or more cell culture vessels is stored (e.g., within an incubator cabinet). For example, one or more cell culture vessel containers (e.g., a rack of cell culture vessel containers) may be stored at a storage location and later transferred to a different location (e.g., an imaging location). The storage location may be disposed in the internal chamber of the incubator cabinet. A storage location may be configured for storing a plurality of cell culture vessel containers (e.g., a rack of cell culture vessel containers). In some embodiments, a storage location may be configured to store cell culture vessel containers horizontally, while in other embodiments it may be configured to store cell culture vessel containers vertically. For example, a storage location may include a plurality of slots to receive cell culture vessels stacked vertically over one another. In some embodiments, each of the plurality of cell culture vessel containers comprise at least one exterior portion configured to interface with a second container. In some embodiments, a plurality of cell culture vessel containers can be physically connected in a modular manner such that a self-supporting rack of cell culture vessel containers is formed. A storage location (e.g., a rack of cell culture vessel containers) may be configured to hold 1, 2, 3, 4, 5, 6, 7, 8, 9, 10, 15, 20, 25, 30, 35, 40, 45, 50, 100, or any other number of cell culture vessel containers. In some embodiments, a storage location may be configured to hold greater than 100 cell culture vessel containers. In some embodiments, each cell culture vessel in a storage location houses cells from a different subject. In some embodiments, a storage location may include a mechanism for moving one or more storage arrays, racks, shelves, pigeon-holes, cubbies, trays, slots, or other positions or mechanisms. For example, a storage location may include one or more motors and movable stages (e.g., an xy or xyz stage) to move a storage rack from one position in an internal chamber to another position in an internal chamber, e.g., to facilitate access to one or more cell culture vessel containers stored in different locations. In some embodiments, the incubator cabinet (e.g., a non-humidified incubator cabinet) may include one or more cell culture vessel container transfer devices for moving one or more cell culture vessel containers.

A storage location may be configured to securely hold or receive one or more cell culture vessel containers. For example, one or more components of the storage location may include one or more locking mechanisms that have one or more adhesive, magnetic, electrical, and/or mechanical components (e.g., snaps, fasteners, locks, clasps, gaskets, o-rings, septa, springs, and other engagement members). In some embodiments, a storage location and/or cell culture vessel container may include one or more grooves or depressions and/or may involve pieces of molded plastic. For example, a cell culture vessel container may include one or more protruded features (e.g., a rim or knob) that is molded for insertion into one or more corresponding grooves, holes, or depressions at a storage location (e.g., a rack of cell culture vessel containers). In some cases, a cell culture vessel container may include one or more grooves, holes, or depressions that are molded to fit one or more corresponding protruded features at a storage location.

In some embodiments, an incubator cabinet (e.g., a non-humidified incubator cabinet) comprises an imager. As used herein, an "imager" refers to an imaging device for measuring light (e.g., transmitted or scattered light), color, morphology, or other detectable parameters such as a number of elements or a combination thereof. An imager may also be referred to as an imaging device. In certain embodiments, an imager includes one or more lenses, fibers, cameras (e.g., a charge-coupled device camera or CMOS camera), apertures, mirrors, filers, light sources (e.g., a laser or lamp), or other optical elements. An imager may be a microscope. In some embodiments, the imager is a bright-field microscope. In other embodiments, the imager is a holographic imager or microscope. In other embodiments, the imager is a fluorescence microscope.

As used herein, a "fluorescence microscope" refers to an imaging device which is able to detect light emitted from fluorescent markers present either within and/or on the surface of cells or other biological entities, said markers emitting light at a specific wavelength in response to the absorption a light of a different wavelength.

As used herein, a "bright-field microscope" is an imager that illuminates a sample and produces an image based on the light absorbed by the sample. Any appropriate bright-field microscope may be used in combination with an incubator cabinet provided herein.

As used herein, a "holographic imager" is an imager that provides information about an object (e.g., sample) by measuring both intensity and phase information of electromagnetic radiation (e.g., a wave front). For example, a holographic microscope measures both the light transmitted after passing through a sample as well as the interference pattern (e.g., phase information) obtained by combining the beam of light transmitted through the sample with a reference beam.

A holographic imager may also be a device that records, via one or more radiation detectors, the pattern of electromagnetic radiation, from a substantially coherent source, diffracted or scattered directly by the objects to be imaged, without interfering with a separate reference beam and with or without any refractive or reflective optical elements between the substantially coherent source and the radiation detector(s).

In some embodiments, an incubator cabinet (e.g., a non-humidified incubator cabinet) includes a single imager. In some embodiments, an incubator cabinet includes two imagers. In some embodiments, the two imagers are the same type of imager (e.g., two holographic imagers or two bright-field microscopes). In some embodiments, the first imager is a bright-field microscope and the second imager is a holographic imager. In some embodiments, an incubator cabinet comprises more than 2 imagers. In some embodiments, cell culture incubators comprise three imagers. In some embodiments, cell culture incubators having 3 imagers comprise a holographic microscope, a bright-field microscope, and a fluorescence microscope.

Figure 9:
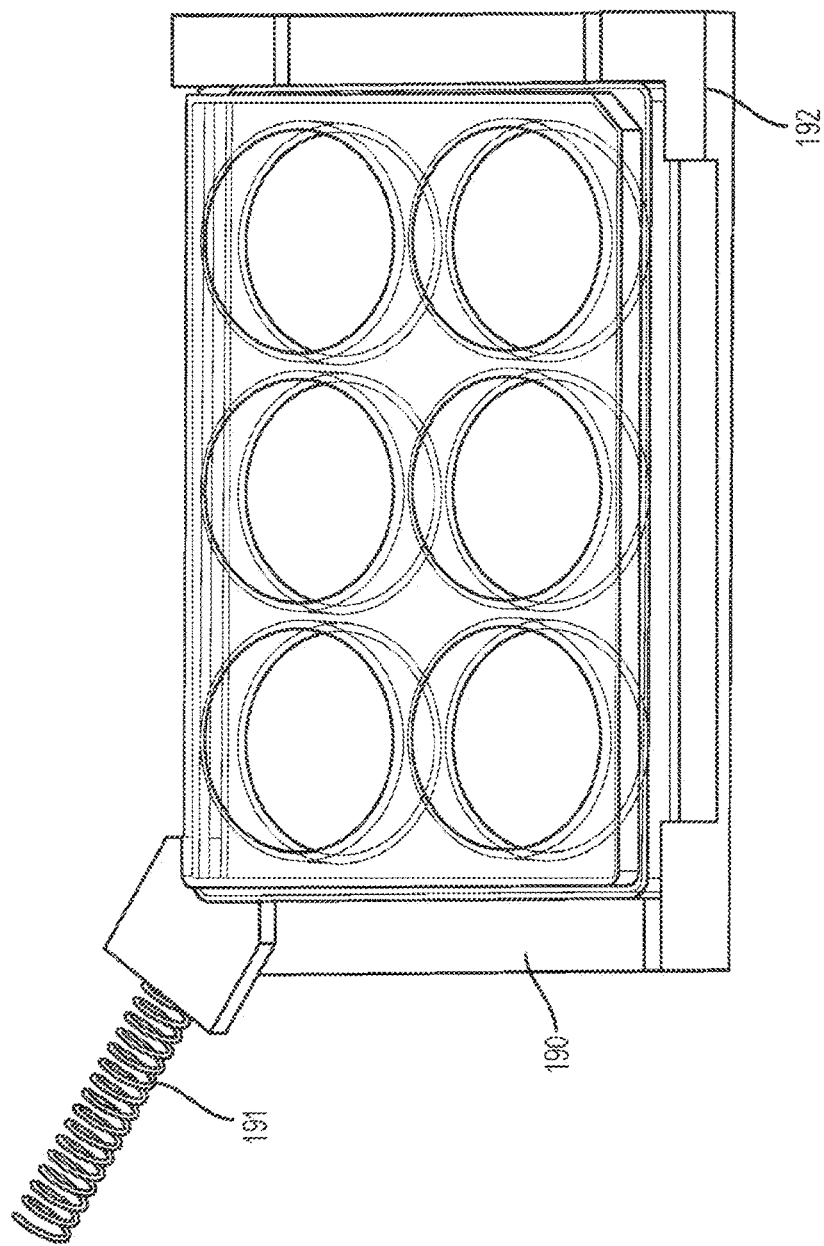
FIG. 9 is a schematic of an illustrative embodiment of a location (e.g., an imaging location or a manipulating location) comprising a spring loaded pusher and a locator.

As used herein, an "imaging location" is the location where an imager images one or more cells. For example, an imaging location may be disposed above a light source and/or in vertical alignment with one or more optical elements (e.g., lens, apertures, mirrors, objectives, and light collectors). In some embodiments, an imaging location comprises a spring loaded pusher and two locators configured to secure a microplate to the location, for example as shown in FIG. 9.

As used herein, a "fiducial mark" refers to a feature that facilitates alignment of one or more components. In some embodiments, fiducial marks may include one or more hole apertures over a fluorescent media or printed or embossed fluorescent material. In other embodiments, fiducial marks may include grids, lines, or symbols. In some embodiments, one or more cell culture vessels include one or more fiducial marks to facilitate alignment of one or more cell culture vessels with an imager. In some embodiments, fiducial marks may be associated with moving parts, including transfer devices and robotics devices.

In some embodiments, a cell culture vessel (e.g., a cell culture vessel housed in a cell culture vessel container described herein) is substantially aligned with an imager. In some embodiments, a cell culture vessel (e.g., a cell culture vessel housed in a cell culture vessel container described herein) is substantially aligned with an imager via the use of at least one fiducial mark. As used herein, the term "substantially aligned" implies that one or more elements are substantially overlapping, identical, and/or in line with one another. The substantial alignment of one or more cell culture vessels (e.g., cell culture vessels each housed in a cell culture vessel container described herein) at one or more locations (e.g., imaging locations) may facilitate the analysis of a sample by permitting overlapping images of the cell culture vessel to be obtained. For example, a cell culture vessel may be imaged at a first imaging location by a first imager and subsequently imaged at a second imaging location by a second imager. If the imaging fields of the respective imagers are substantially aligned, the images recorded by the first and second imagers may be combined ("stitched together") for analysis. One or more fiducial marks present on one or more cell culture vessels may facilitate substantial alignment. In some cases, one or more fiducial marks present at one or more imaging or other locations (e.g., manipulation or maintenance locations) may facilitate substantial alignment.

As used herein, a "manipulator for manipulating cells" refers to a device for manipulating cells in the internal chamber. The manipulator may include one or more needles, capillaries, pipettes, and/or micromanipulators. For example, the manipulator may include a cell picker. A manipulator for manipulating cells may operate by detecting desirable cells or groups thereof present at a first location based on a predetermined criterion and transferring the desired cells or groups thereof from the first location to a second location. A cell picker may detect, pick, and/or transfer desirable or undesirable (e.g., pre-differentiated cell weeding) cells or groups thereof based on a manual or automated analysis. In some embodiments, information produced by an imager may be analyzed to detect desirable or undesirable cells. The cell picker may then transfer the desirable or undesirable cells to the second location. For example, an imager may image cells in or on a cell culture vessel at an imaging location, and the image used to identify desirable or undesirable cells or groups thereof. The cell picker may then transfer the desirable or undesirable cells, e.g., by contacting each desired cell or cells with a needle, capillary, pipette, or micromanipulator and effecting a movement of the cell or cells, from their first location to a second location in or on the cell culture vessel or elsewhere in the internal chamber. In some embodiments, the first location of the cells may be in or on a cell culture vessel. In particular embodiments, a cell picker transfers cells from a first location in or on a cell culture vessel to a second location on the same cell culture vessel. In other embodiments, a cell picker transfers cells from a first location in or on a first cell culture vessel to a second location in or on a second cell culture vessel. In certain other embodiments, a cell picker transfers cells from a first location in or on a cell culture vessel to a second location in the internal chamber that is not in or on a cell culture vessel.

In some embodiments, the manipulator includes at least one microelectrode. As used herein, the term "microelectrode" refers to an electrical conductor used to deliver electrical stimulation to a cell. For example, microelectrodes can be used to deliver genetic material into a cell by electroporation. In some embodiments, the manipulator includes at least one microinjector. Generally, microinjectors are glass micropipettes that have been pulled to form a sharp, hollow structure capable of piercing the membrane of a cell and serving as a conduit for the introduction of genetic material into the cell. In some embodiments, cell cultures are manipulated in other ways during culture in incubators and vessels described herein. For example, cell cultures may be transfected with nucleic acids (e.g., DNA or RNA) or exposed to viral infection (e.g., using recombinant virus particles to deliver DNA or RNA).

In some embodiments, a manipulator includes fluid handling devices. For example, a manipulator may include one or more liquid dispensing apparatus, such as pipette tip holders or a cell printing device. In some embodiments fluid handling devices are automated. In some aspects, manipulators having automated fluid handling systems that dispense growth media from fluid storage vessels located inside the internal chamber of the incubator to cell culture vessel can be used.

In some embodiments (e.g., for adherent cell cultures), culture media can be removed directly by aspiration and replaced with fresh media. In some embodiments (e.g., for non-adherent/suspension cultures), media changes can involve centrifuging a cell culture, removing the old culture media and replacing it with fresh media. In some embodiments, the centrifuge is located in the internal chamber of an incubator. In some embodiments, culture vessels allow for continuous media replacement. In some embodiments, the incubators described herein may include one or more components that can be used to process, replace, supply, and/or maintain different aspects of a culture media to support cells. Incubators may include a reservoir containing waste media and/or a reservoir containing fresh media. Such reservoirs may be present (e.g., for temporary storage) within a refrigerator inside the incubator or a refrigerated section of the incubator. In some embodiments, one or more reservoirs are provided outside the incubators and piping is provided into and out from the incubator space to supply or draw from a liquid handler units (e.g., liquid handle units having an aspirator) or temporary reservoir within the incubator to facilitate cells feeding, media changes, and other related needs. For suspension cells, devices may be provided within the incubator to separate cells from waste media (e.g., centrifuge(s) to facilitate cell pelleting) to facilitate automated media changes as part of an incubator provided herein. In some embodiments, the document provides a system comprising a cell culture incubator connected to a computer, capable of automatically monitoring and adjusting cell culture conditions for optimal growth of the cell culture.

In some embodiments, cells are passaged within an incubator described herein. In some embodiments, a cell culture is split, and a subset of the cell culture is transferred to a fresh culture vessel for further growth. In some embodiments (e.g., for adherent cell cultures), cells are detached (e.g., mechanically, for example, using gentle scraping, and/or enzymatically, for example, using trypsin-EDTA or one or more other enzymes) from a surface prior to being transferred to a fresh culture vessel. In some embodiments (e.g., for suspension cell cultures), a small volume of a cell culture is transferred to a fresh culture vessel.

In some embodiments, a manipulator is manually operated. For example, a manipulator having a fluid handling system located inside the internal chamber of an incubator cabinet may be electronically-linked to and controlled by a user-directed joystick located outside the internal chamber of the incubator cabinet. In some embodiments, the user-directed joystick is connected to a display device. In some embodiments, the display device shows images captured by an imaging device inside the internal chamber of the incubator cabinet.

In some embodiments, a manipulator is automated. For example, a manipulator inside an internal chamber of an incubator cabinet may be electronically connected to a controller outside of the incubator cabinet that directs the manipulator. In some embodiments, the computer automatically remembers where particular cell culture vessels are located inside the incubator. In some embodiments, the computer uses barcodes or other identifying information to verify that the said locations are correctly remembered.

One or more elements of the manipulator for manipulating cells may be sterilized, for example using a sterilizing composition or method (e.g., ethanol or ozone gas), prior to manipulation.

As used herein, "manipulation location" refers to the location at which cells are manipulated by a manipulator for manipulating cells (e.g., a cell picker). In some embodiments, a manipulation location comprises a spring loaded pusher and two locators configured to secure a microplate to the location, for example as shown in FIG. 9. In certain embodiments, the manipulation location may be the same as the imaging location.

According to one aspect, the cell culture incubator includes an incubator cabinet with an imaging location and a manipulating location. Cells of a cell culture vessel are imaged at the imaging location by an imager and manipulated at the manipulating location by a manipulator. In some embodiments, the imaging location and the manipulating location are two distinct locations within the incubator cabinet. The cell culture incubator may include a transfer device that moves cell culture vessels between the imaging location and the storage location. In other embodiments, the imaging location and the manipulating location are the same, such that the cells of culture vessels are imaged at the manipulation location.

In some embodiments, an imager may be used in conjunction with a manipulator. For example, an imager may image cells in or on a cell culture vessel at an imaging location, and the image used to identify desirable cells or groups thereof. The manipulator may then transfer the desirable cells, e.g., by contacting each desired cell or cells with a needle, capillary, pipette, or micromanipulator and effecting a movement of the cell or cells, from their first location to a second location in or on the cell culture vessel or elsewhere in the internal chamber. In some embodiments, the manipulator aseptically transfers growth media, growth factors, or expression vectors into cell culture vessels.

In some embodiments, a single location within the incubator cabinet (e.g., a non-humidified incubator cabinet) may serve as an imaging location and a manipulating location. In some embodiments, an imaging location and a manipulating location are at different locations within the incubator cabinet. In one embodiment, cells are imaged as they are manipulated by the manipulator.

In some embodiments, the environment inside an incubator or a cell culture vessel container is controlled by a control system that may be configured to control the temperature, humidity, carbon dioxide, oxygen and other gaseous components ((e.g., sterilization gases, such as, ozone, and hydrogen peroxide)) inside the incubator (e.g., in one or more internal chambers). In some embodiments, a control system controls the environmental conditions (e.g., temperature, humidity, carbon dioxide, oxygen and other gaseous components) within each internal chamber separately. For example, in order to protect sensitive mechanical, electronic and optical components, the humidity of an internal chamber may be maintained at a lower level than an internal chamber having a storage location. In some embodiments, the incubator or cell culture vessel container is further provided with a monitoring system with predefined sensors. Examples of monitoring devices include but are not limited to oxygen monitors, carbon dioxide monitors, ozone gas detectors, hydrogen peroxide monitors and multi gas monitors. For example, in some embodiments, an incubator advantageously includes a plurality of sensors responsive to different parameters relevant to cell growth, which may include temperature, air purity, contaminant levels, pH, humidity, $N_2$, $CO_2$, $O_2$ and light. By means of this monitoring system, parameters in the incubator can be measured using sensors for the duration of a culture or process. In some embodiments, parameters measured by the sensors are transmitted by the monitoring system via a line to a computer-controlled monitoring and control system for further processing as discussed elsewhere herein.

In some embodiments, an environmental monitoring system can be used in conjunction with an incubator or cell culture vessel container described herein. In some embodiments, one or more sensors that provide for the measurement of temperature, air composition (e.g., $CO_2$ concentration, $O_2$ concentration, etc.), and/or humidity of the system can be associated with an incubator or cell culture vessel container (e.g., fitted within an incubator cabinet or within a cell culture vessel container). In some embodiments, one or more such sensors can be incorporated as part of an incubator or cell culture vessel container (e.g., attached to, integral to, or otherwise connected to an internal wall or door of the incubator or cell culture vessel container). In some cases, one or more sensors can be positioned at any suitable location(s) outside or inside an incubator cabinet (e.g., within a transfer chamber and/or an internal chamber, for example attached to an internal wall, and/or upper or lower internal surface).

In some embodiments, a gas sensor is provided that can provide a reading in real time of the concentration of gas in contact with the sensor (e.g., gas in a cabinet, or ambient air) in percent, parts per million, or any other standard unit. Gas sensors for use in the methods and incubators provided herein include $CO_2$ sensors, $O_2$ sensors, $N_2$ sensors, ozone gas detectors, hydrogen peroxide monitors, multi gas monitors, and CO sensors. Such sensors are available from a number of commercial sources. In some cases, the environment of the incubator may be modulated or controlled based upon the information provided by the sensors described herein. For example, the level of $CO_2$ in an incubator may be increased upon indication from a $CO_2$ sensor that a lower than desirable concentration of $CO_2$ is present in the incubator.

In some embodiments, one or more heating or cooling elements can be incorporated within the incubator (e.g., on an inner surface of the cabinet or door, and/or integrated within one or more of the walls and/or the base of the cabinet) for purposes of controlling the temperature within the incubator. In some embodiments, a heating element can be used for thawing liquids, for example, cell culture media or other reagents.

In some embodiments, one or more air or oxygen sources, carbon filters, and/or one or more dehumidification systems are connected to the incubator and configured to control the level of oxygen, carbon dioxide, and/or humidity within the incubator (e.g., in response to signals from the one or more sensors in or attached to the incubator). In some embodiments, one or more controllers are attached to the sensors and other systems to control the internal environment of the incubator.

In some embodiments, an incubator can include one or more light sources (e.g., an incandescent bulb, LED, UV, or other light source). These can be placed within the incubator to illuminate regions within the cabinet. In some embodiments, the culture system operation is monitored using a camera or other light sensitive device that can be placed within or outside the incubator. In some embodiments, the light source is a sterilizing light source. For example, a UV lamp may be located within the transfer chamber and/or the interior chamber of an incubator provided herein.

In some embodiments, the incubator includes a transparent object (e.g., window) that allows visible light or other light wavelengths from within the incubator to be detected by a camera or other light sensitive device placed outside the incubator.

In some embodiments, a sensor or other feature is provided to detect when one or more doors of an incubator are opened (e.g., when an incubator cabinet door, such as an external or internal door, is opened). Such features are useful because they allow operators to keep track of or be warned of any unscheduled or unauthorized openings of the incubator (e.g., the incubator cabinet) that could jeopardize sterility, spoil a production, compromise an assay or experiment, etc.

In some embodiments, a radiofrequency beacon or other signal source is located within the incubator (e.g., within the incubator cabinet) that can be used to determine the location of one or more devices within the incubator cabinet (e.g., devices having sensors that can detect the signal and use it to determine their location). In some embodiments, the devices could have signal sources and the sensor(s) could be located within one or more of the chambers of an incubator cabinet (e.g., located on an internal surface of an internal chamber).

In some embodiments, light signals or lasers (e.g., a grid of laser signals) can be used to determine the location and/or identity of one or more devices or components within the incubator cabinet. Such information can be communicated, e.g., wired or wirelessly, to an external computer or monitoring station. The information can be used to control operation of a transfer device, e.g., a robotic arm, within the incubator cabinet to ensure that the transfer device can grab, manipulate, or maneuver devices or items appropriately within the incubator cabinet.

In some embodiments, before containers or vessels are brought into an incubator cabinet, a user can select an automation system protocol based on the particular containers, vessels, ingredients, or cells that are being inserted into the incubator cabinet. Relevant information related to the incubator and/or one or more incubator components, and the cells being grown can be entered into a data system. For example, one or more identifiers such as barcodes (e.g., 1D or 2D barcodes) can be placed on the container or vessel and other significant information, such as, the type of container, the contents of the container and, what assays or manipulations are to be performed on the sample in the container can be specified. In some embodiments, information related to the incubator system and/or cells can be contained in one or more barcodes, on a separate data system, or a combination thereof. The user may also enter information that identifies the dimensionality (e.g., height, diameter) of the vessel or other container or the system itself determine measure the height of the vessel or other container. Using this information, the robotic arm may be requested to transport a particular container, such as when an analytical module is ready to perform an assay or other manipulation on cells grown in the vessels or has completed performing an assay or manipulation.

Computer and Control Equipment

The incubators provided herein include several components, including sensors, environmental control systems, robotics, etc. which may operate together at the direction of a computer, processor, microcontroller or other controller. The components may include, for example, a transfer device (e.g., robotic arm), a liquid handling devices, a delivery system for delivering culture vessels or cell culture vessel containers, or other components to or from the incubator cabinet, an environmental control system for controlling the temperature and other environmental aspects of the incubator cabinet, a door operation system, an imaging or detection system, and a cell culture assay system.

In some cases, operations such as controlling operations of a cell culture incubator and/or components provided therein or interfacing therewith may be implemented using hardware, software or a combination thereof. When implemented in software, the software code can be executed on any suitable processor or collection of processors, whether provided in a single component or distributed among multiple components. Such processors may be implemented as integrated circuits, with one or more processors in an integrated circuit component. A processor may be implemented using circuitry in any suitable format.

A computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable, mobile or fixed electronic device, including the incubator itself.

In some cases, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. In other examples, a computer may receive input information through speech recognition or in other audible format, through visible gestures, through haptic input (e.g., including vibrations, tactile and/or other forces), or any combination thereof.

One or more computers may be interconnected by one or more networks in any suitable form, including as a local area network or a wide area network, such as an enterprise network or the Internet. Such networks may be based on any suitable technology and may operate according to any suitable protocol and may include wireless networks, wired networks, or fiber optic networks.

The various methods or processes outlined herein may be coded as software that is executable on one or more processors that employ any one of a variety of operating systems or platforms. Such software may be written using any of a number of suitable programming languages and/or programming or scripting tools, and may be compiled as executable machine language code or intermediate code that is executed on a framework or virtual machine.

One or more algorithms for controlling methods or processes provided herein may be embodied as a readable storage medium (or multiple readable media) (e.g., a computer memory, one or more floppy discs, compact discs (CD), optical discs, digital video disks (DVD), magnetic tapes, flash memories, circuit configurations in Field Programmable Gate Arrays or other semiconductor devices, or other tangible storage medium) encoded with one or more programs that, when executed on one or more computers or other processors, perform methods that implement the various methods or processes described herein.

In some embodiments, a computer readable storage medium may retain information for a sufficient time to provide computer-executable instructions in a non-transitory form. Such a computer readable storage medium or media can be transportable, such that the program or programs stored thereon can be loaded onto one or more different computers or other processors to implement various aspects of the methods or processes described herein. As used herein, the term "computer-readable storage medium" encompasses only a computer-readable medium that can be considered to be a manufacture (e.g., article of manufacture) or a machine. Alternatively or additionally, methods or processes described herein may be embodied as a computer readable medium other than a computer-readable storage medium, such as a propagating signal.

The terms "program" or "software" are used herein in a generic sense to refer to any type of code or set of executable instructions that can be employed to program a computer or other processor to implement various aspects of the methods or processes described herein. Additionally, it should be appreciated that according to one aspect of this embodiment, one or more programs that when executed perform a method or process described herein need not reside on a single computer or processor, but may be distributed in a modular fashion amongst a number of different computers or processors to implement various procedures or operations.

Executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in various embodiments.

Also, data structures may be stored in computer-readable media in any suitable form. Non-limiting examples of data storage include structured, unstructured, localized, distributed, short-term and/or long term storage. Non-limiting examples of protocols that can be used for communicating data include proprietary and/or industry standard protocols (e.g., HTTP, HTML, XML, JSON, SQL, web services, text, spreadsheets, etc., or any combination thereof). For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags, or other mechanisms that establish relationship between data elements.

In some embodiments, information related to the operation of the incubator (e.g., temperature, humidity, gas composition, images, cell culture conditions, etc., or any combination thereof) can be obtained from one or more sensors associated with the incubator (e.g., located within the incubator cabinet, or located within the incubator but outside the incubator cabinet), and can be stored in computer-readable media to provide information about conditions during a cell culture incubation. In some embodiments, the readable media comprises a database. In some embodiments, said database contains data from a single incubator. In some embodiments, said database contains data from a plurality of incubators. In some embodiments, data is stored in a manner that makes it tamper-proof. In some embodiments, all data generated by the instrument (e.g., an incubator) is stored. In some embodiments, a subset of data is stored.

In some embodiments, the component (e.g., a computer) controls various processes performed inside the incubator. For example, a computer may direct control equipment (e.g., a manipulator, an imager, a fluid handling system, etc.). In some embodiments, the computer controls imaging of cell cultures, picking of cells, weeding of cells (e.g., removal of cell clumps), monitoring of cell culture conditions, adjustment of cell culture conditions, tracking of cell culture vessel movement within the incubator, and/or scheduling of any of the foregoing processes.

Figure 1B:
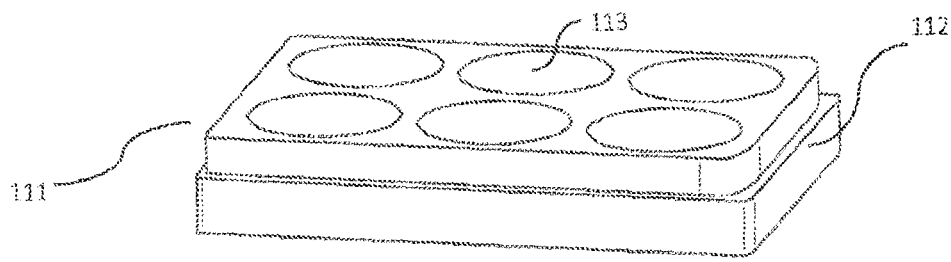
Figure 1C:
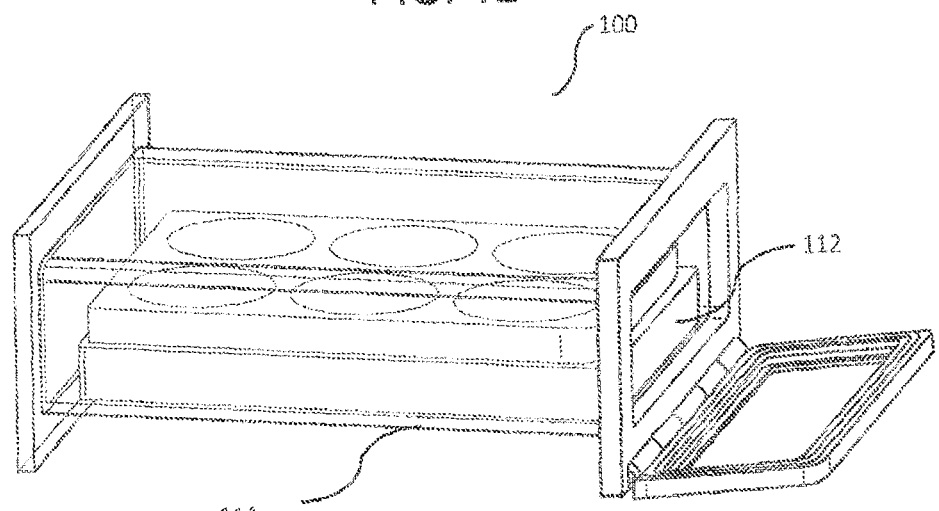

Turning to the figures, FIGS. 1A-1C are schematics of illustrative embodiments of a selectively permeable cell culture vessel storage container. FIG. 1A shows a schematic of an illustrative embodiment of a selectively permeable cell culture vessel storage container (100) comprising a compartment (101). In some embodiments, at least one wall (102) of the container comprises a gas permeable membrane that is selectively impermeable to water vapor (103). The gas permeable membrane-wall interface is described in further detail in FIG. 7. The at least one wall (102) physically interfaces with a support structure (104). In some embodiments, the support structure interfaces with a surface of the container (105) having an passage (106) to the compartment interior (101). In some embodiments, the container comprises a moveable structure (107) configured for opening and closing the passage. In some embodiments, the movable structure (107) comprises a seal (108) configured to interface with the surface of the container that surrounds the passage (106). The movable structure may interface with the surface via a hinge (109). In some embodiments, the movable structure (107) has an optically transparent surface (110). FIG. 1B shows a schematic of an illustrative embodiment of a cell culture vessel (111), comprising a base (112) and cell culture wells (113). Although depicted as a 6-well plate, the skilled artisan recognizes that any suitable cell culture plate can be housed in the containers described herein. For example, the cell culture vessel can be a cell culture dish (e.g., a 5 cm plate, 10 cm plate, or 25 cm plate) or a multiwell culture plate (e.g., 6 well plate, 12 well plate, 24 well plate, 96 well plate, 384 well plate, 1536 well plate). FIG. 1C shows a schematic of an illustrative embodiment of a selectively permeable cell culture vessel storage container (100) housing a cell culture vessel (111), in which the base of the cell culture vessel (112) interfaces with the bottom surface of the container (114). Although not numbered, the top and side walls of the container are depicted in FIG. 1C, demonstrating that the cell culture vessel (111) is housed within the compartment (101) of the container (100).

Figure 2:
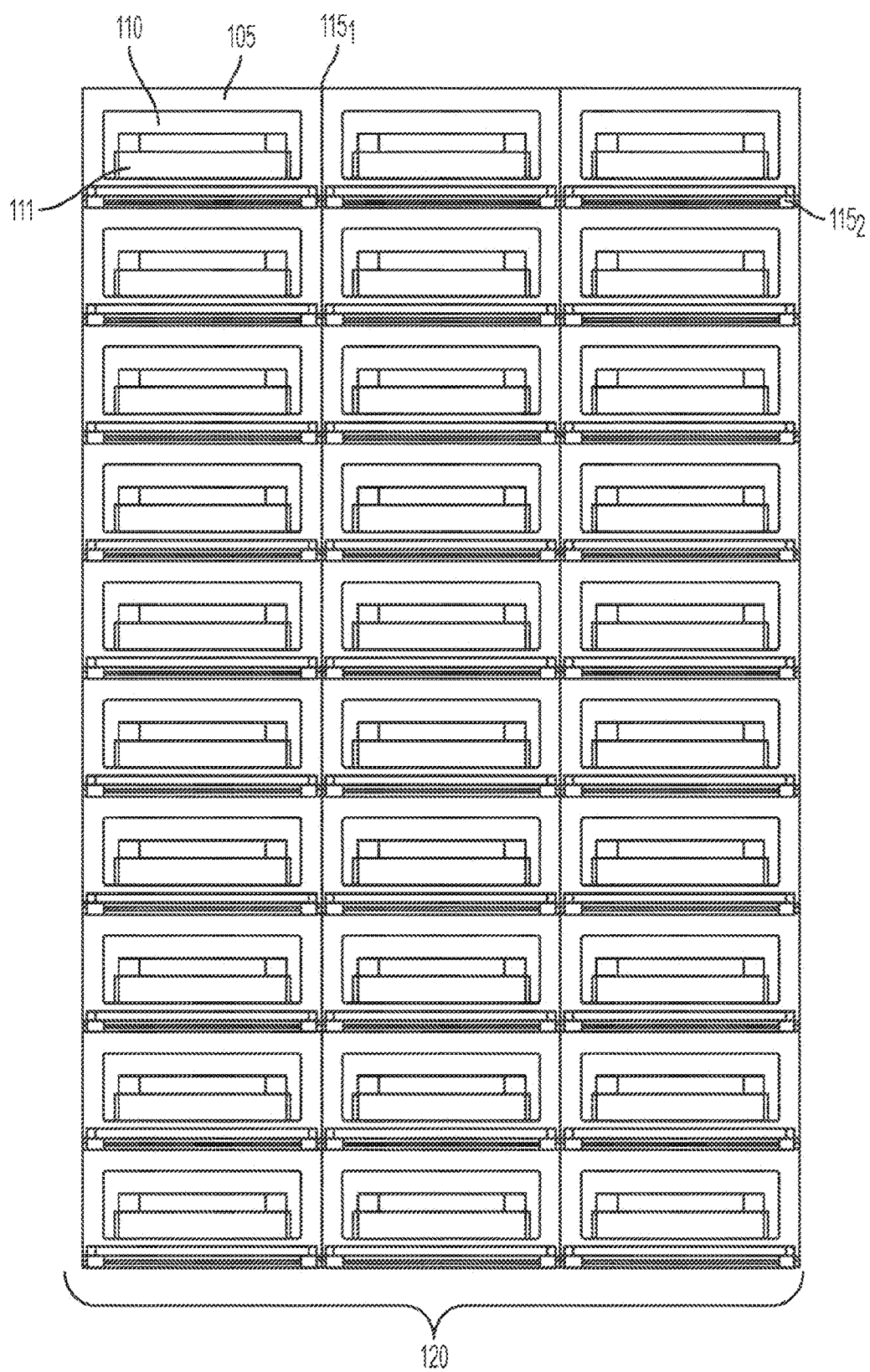
FIG. 2 is a schematic of a front view of an illustrative embodiment of a plurality of selectively permeable cell culture vessel storage containers arranged into a "rack system".

FIG. 2 is a schematic of a front view of an illustrative embodiment of a plurality of selectively permeable cell culture vessel storage containers arranged into a "rack" (120). In some embodiments, each container of the plurality of containers comprises at least one exterior portion configured to interface with a second container. For example, ($115_1$) and ($115_2$) in FIG. 2 depict two separate interfaces formed between containers.

Figure 3:
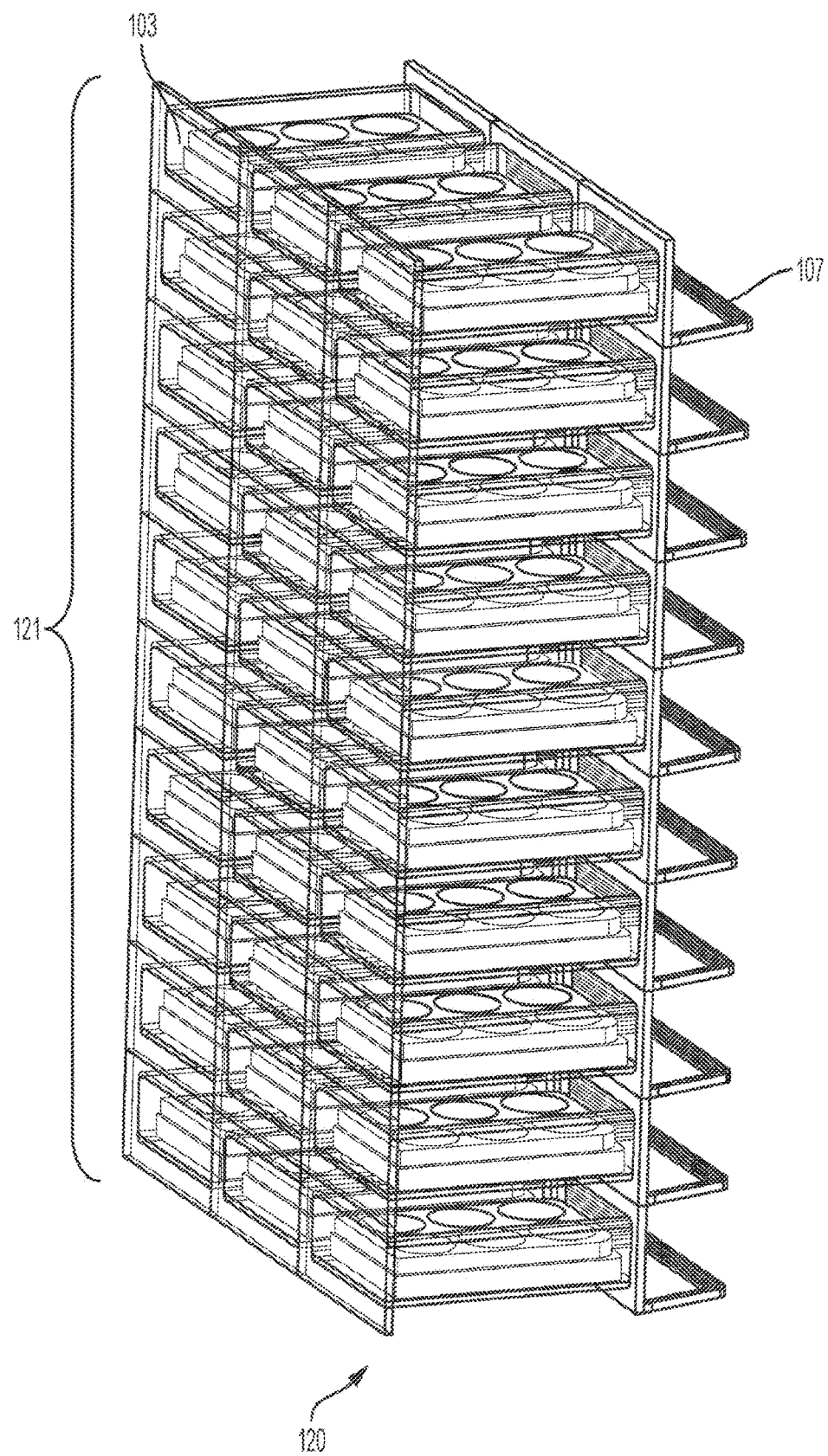
FIG. 3 is a schematic of an oblique view of an illustrative embodiment of a plurality of selectively permeable cell culture vessel storage containers arranged into a "rack".

FIG. 3 is a schematic of an oblique view of an illustrative embodiment of a plurality of selectively permeable cell culture vessel storage containers arranged into a rack (120). In some embodiments, each container of the plurality has a separate gas permeable membrane that is selectively impermeable to water vapor (103). However, in some embodiments, all the containers of the plurality share a single gas permeable membrane that is selectively impermeable to water vapor. For example, a single gas permeable membrane may cover the entire back wall (121) of the rack (120).

Figure 4:
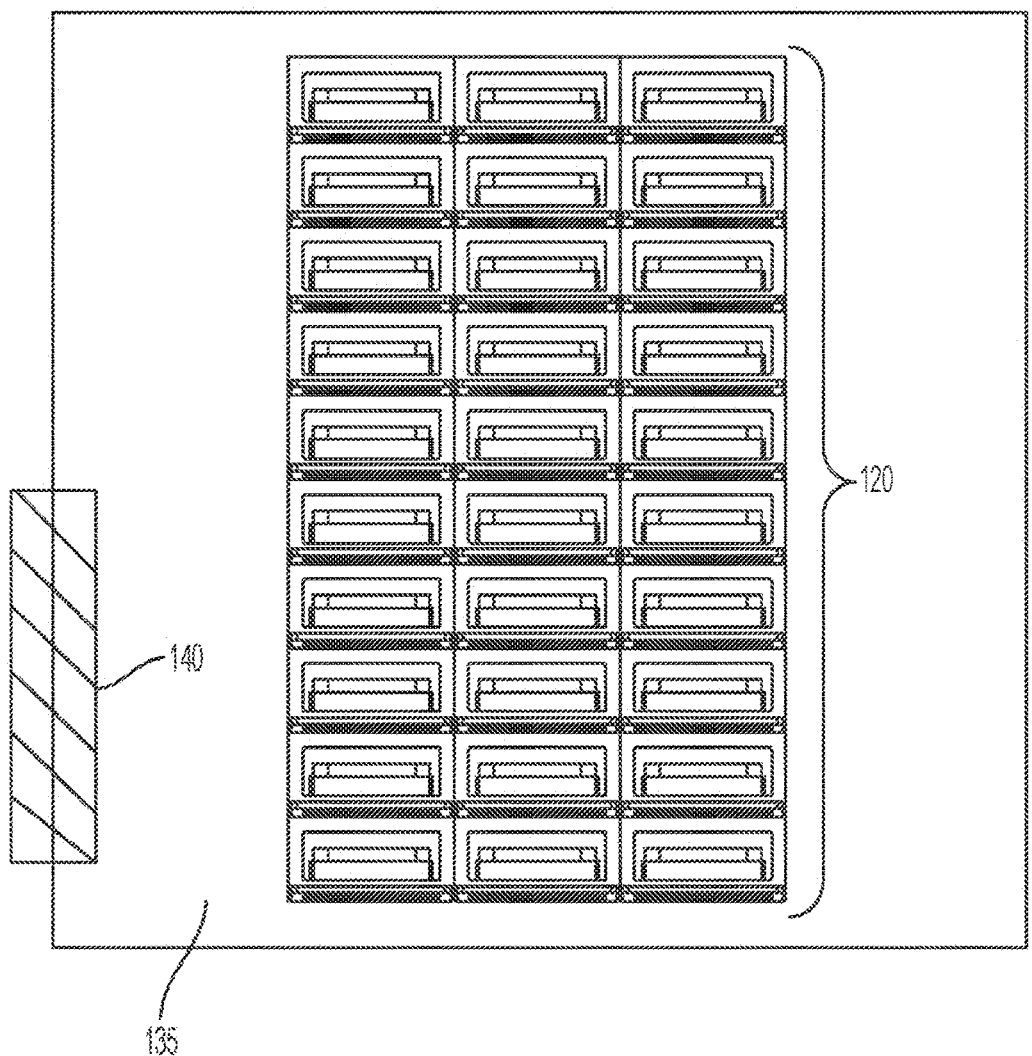
FIG. 4 is a schematic of an illustrative embodiment of a cell culture system comprising an incubator cabinet comprising an internal chamber having an external door, and a rack of selectively permeable cell culture vessel storage containers.

FIG. 4 is a schematic of an illustrative embodiment of a cell culture system comprising an incubator cabinet comprising an internal chamber (135) having an external door (140), and a rack of selectively permeable cell culture vessel storage containers (120). In some embodiments, the internal chamber of the incubator cabinet is a non-humidified environment.

Figure 5:
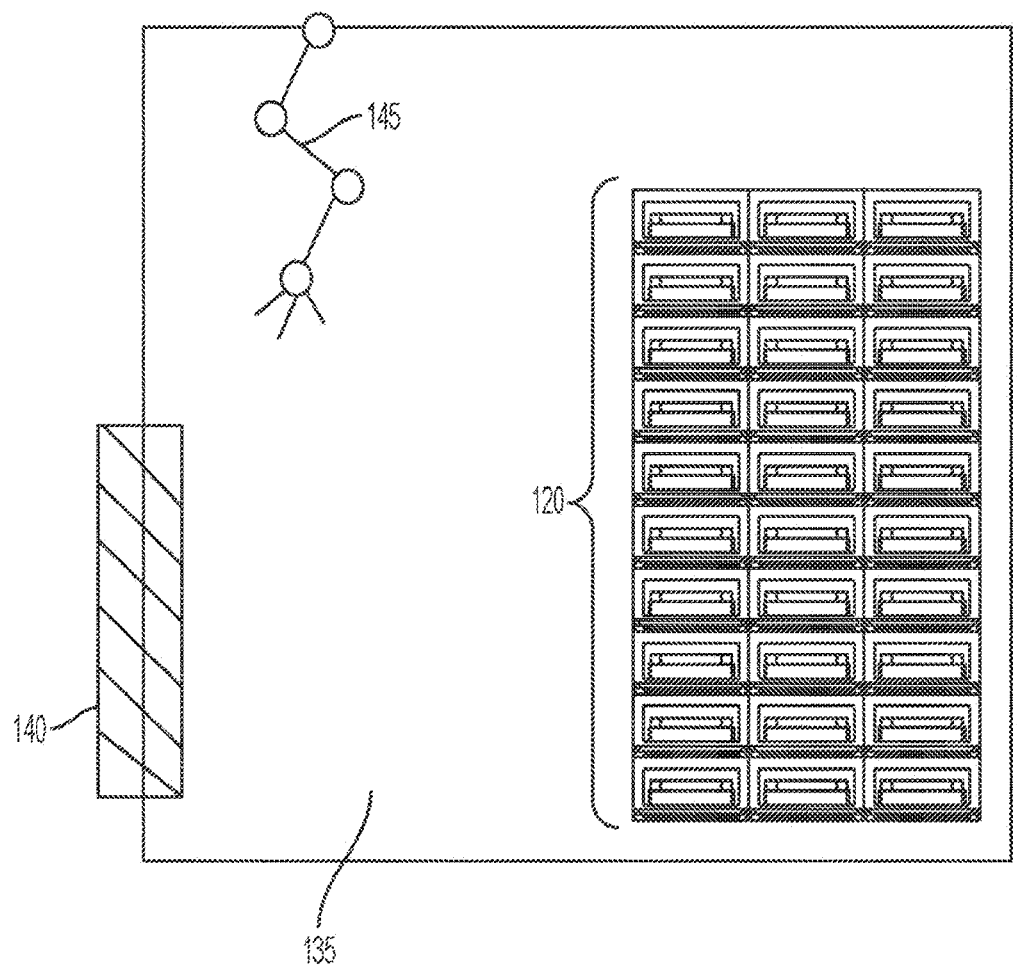
FIG. 5 is a schematic of an illustrative embodiment of a cell culture system comprising an incubator cabinet comprising an internal chamber having an external door, a transfer device, and a rack of selectively permeable cell culture vessel storage containers.

FIG. 5 is a schematic of an illustrative embodiment of a cell culture system comprising an incubator cabinet comprising an internal chamber (135) having an external door (140), a cell culture vessel container transfer device (145), and a rack of selectively permeable cell culture vessel storage containers (120). In some embodiments, the internal chamber of the incubator cabinet is a non-humidified environment.

Figure 6:
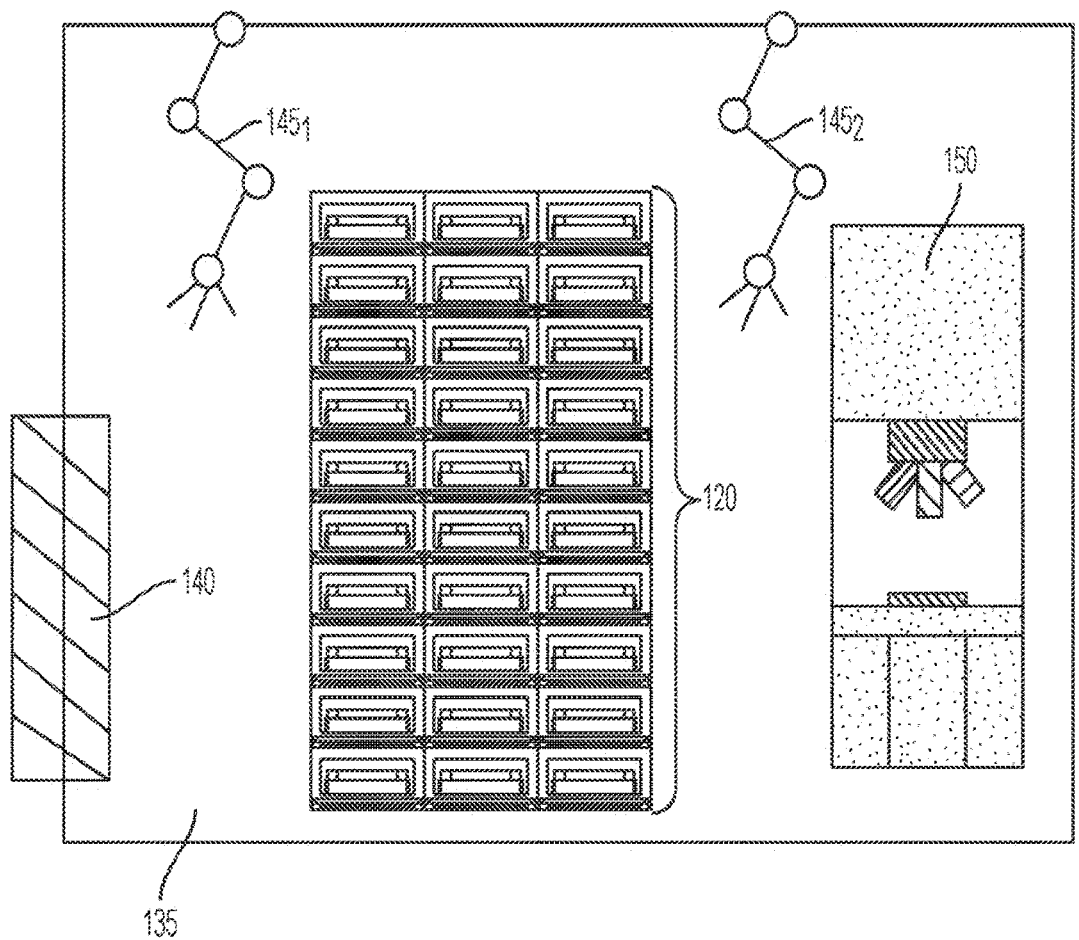
FIG. 6 is a schematic of an illustrative embodiment of a cell culture system comprising an incubator cabinet comprising an internal chamber having an external door, two transfer devices, a rack of selectively permeable cell culture vessel storage containers, and an imager.

FIG. 6 is a schematic of an illustrative embodiment of a cell culture system comprising an incubator cabinet comprising an internal chamber (135) having an external door (140), two transfer devices ($145_1$ and $145_2$), a rack of selectively permeable cell culture vessel storage devices (120), and an imager (150). In some embodiments, the internal chamber of the incubator cabinet is a non-humidified environment.

Figure 7:
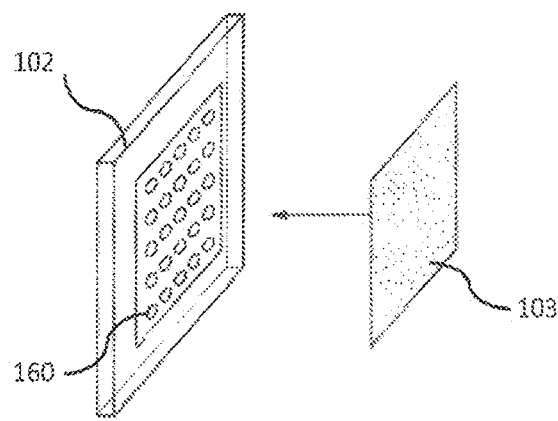
FIG. 7 is a schematic of an illustrative embodiment of an interface between a side of a selectively permeable cell culture vessel storage container and a selectively permeable membrane.

FIG. 7 is a schematic of an illustrative embodiment of an interface (represented by the arrow) between a wall of a selectively permeable cell culture vessel storage container (102) and a gas permeable membrane that is selectively impermeable to water vapor (103). In some embodiments, the wall of the container (102) comprises at least one passage (160) that is configured to be covered by the gas permeable membrane (103).

Figure 8A:
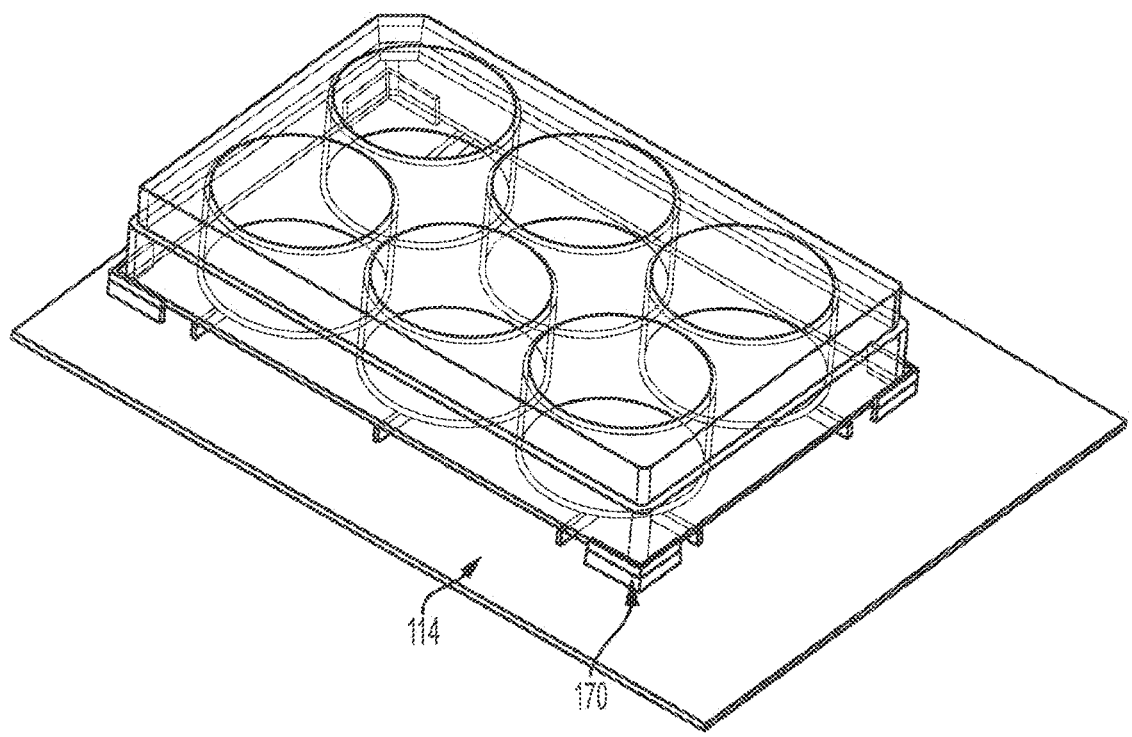
FIGS. 8A-8B are a schematic of an illustrative embodiment of a selectively permeable cell culture vessel storage container having microplate retention devices (e.g., one or more "feet" and/or "locators") attached to the floor of the container.
Figure 8B:
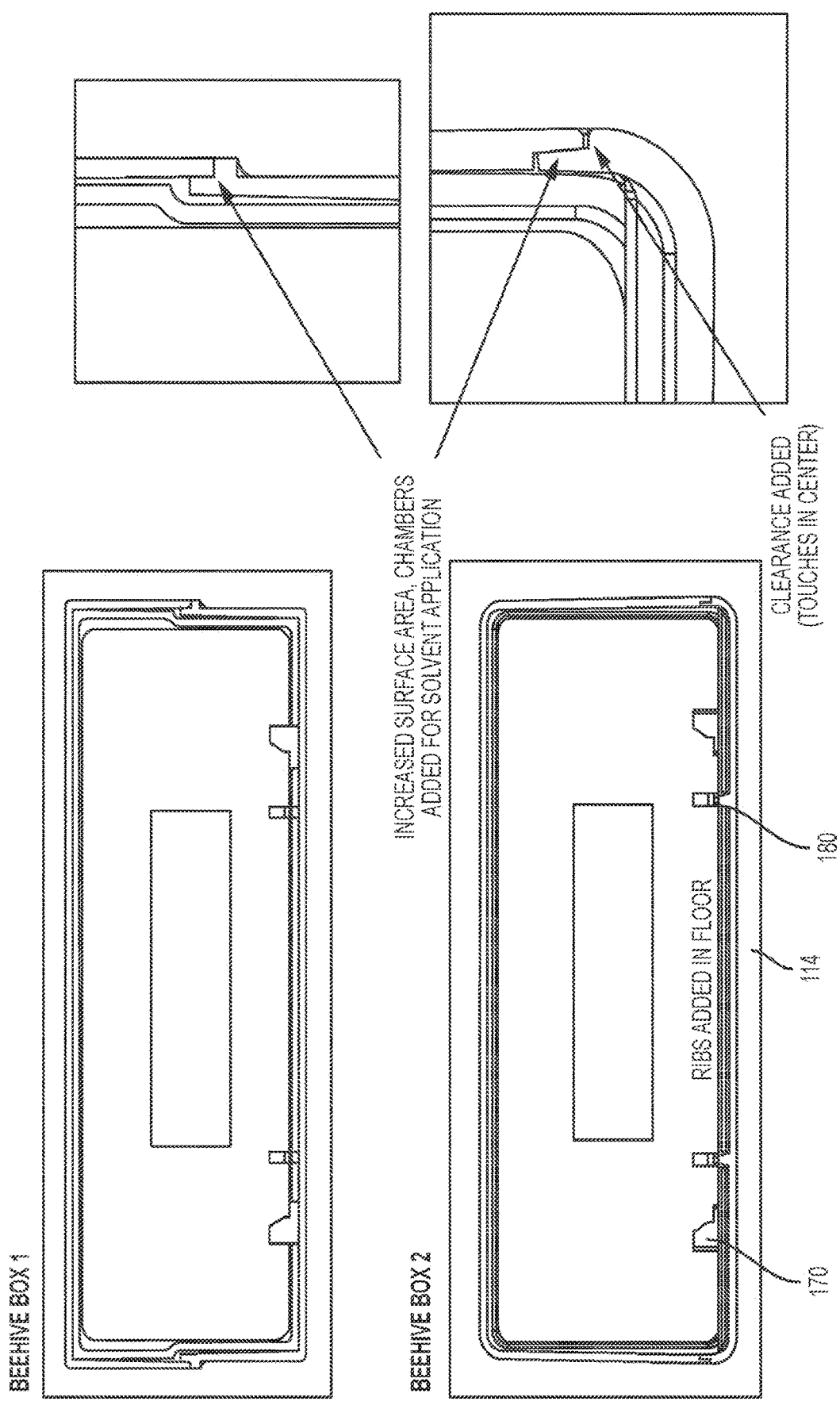

FIG. 8A depicts a microplate resting on top of the feet and locators (e.g., 170) on the bottom surface (114) of a selectively permeable cell culture vessel storage container. FIG. 8B depicts non-limiting embodiments of two selectively permeable cell culture vessel storage containers; the container on the top comprises feet (170) on the bottom surface (114) of the container; the container on the bottom comprises feet (170) and ribs (180). In some embodiments, ribs placed on the floor of the selectively permeable cell culture vessel storage container enable a transfer device (e.g., a grabber, etc.) to prevent a cell culture vessel from interfacing directly with (e.g., touching) the bottom surface of the container. Non-limiting embodiments of side bond joints are also depicted in FIG. 8B.

FIG. 9 is a schematic of an illustrative embodiment of a location (190), such as an imaging location or a manipulating location, comprising a spring loaded pusher (191) and a locator (192). In some embodiments, the pusher and locator are configured to secure a microplate to the location such that the microplate does not move during manipulation (e.g., cell picking) or imaging.

Figure 10:
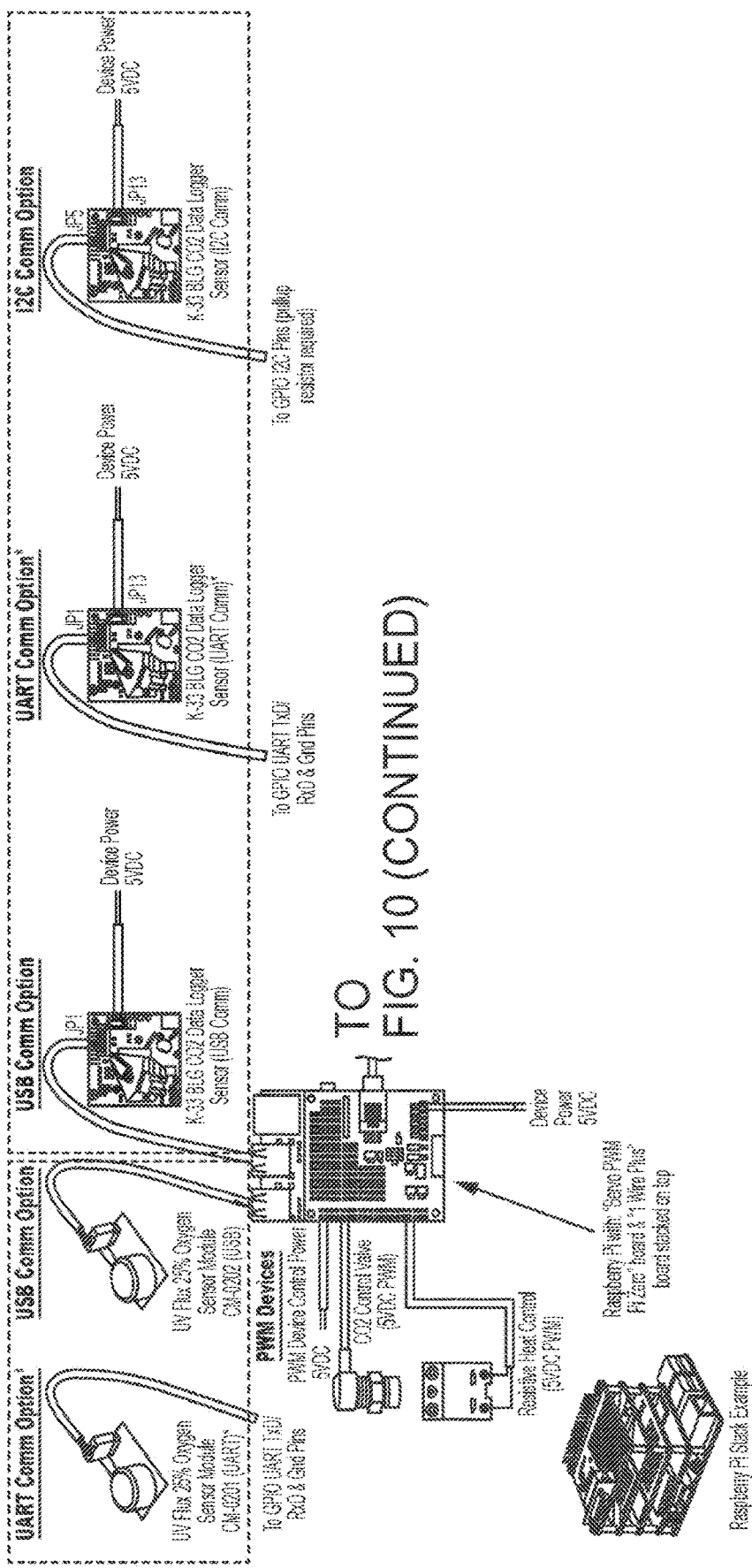
FIG. 10 is a schematic of illustrative embodiments of communication device components (e.g. sensors, environmental control systems, robotics, etc.).
Figure 10:
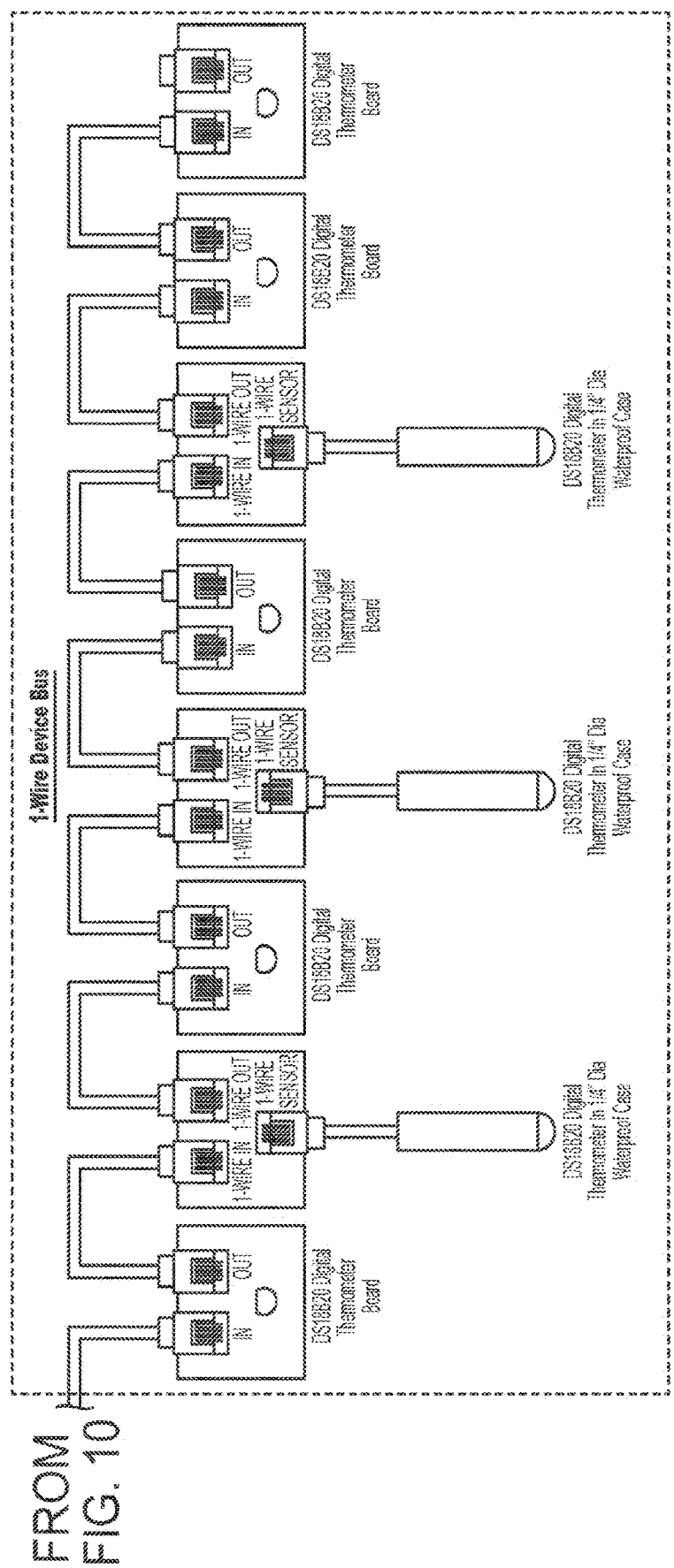

FIG. 10 is a schematic of illustrative embodiments of communication devices (e.g. sensors, environmental control systems, robotics, etc.). Briefly, examples of oxygen sensors, data logger sensors, pulse width modulation (PWM) device controllers and a 1-wire device Bus are depicted.

Figure 11A:
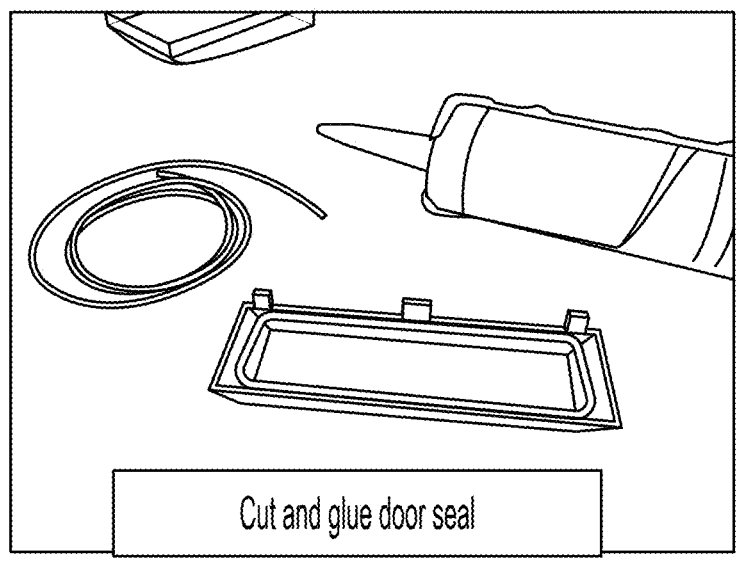
FIGS. 11A-11G provide a non-limiting example of assembly of a selectively permeable cell culture vessel storage container.
Figure 11B:
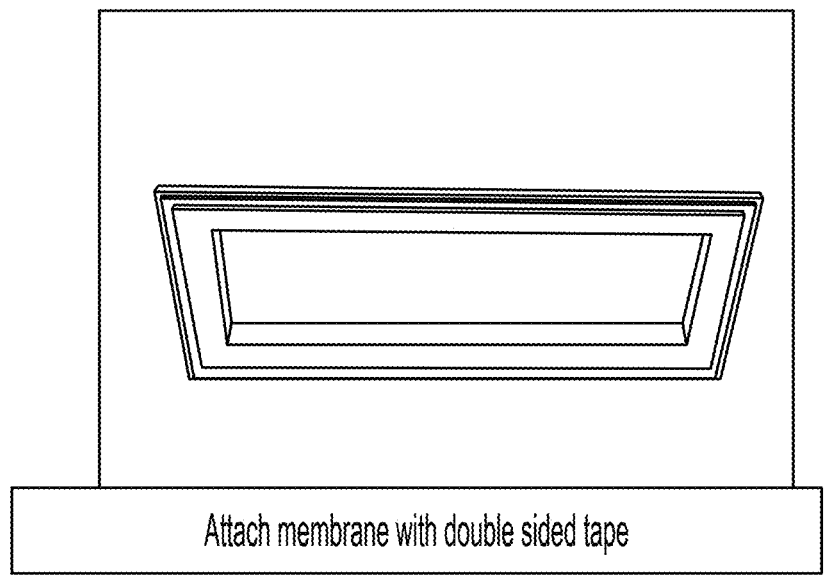
Figure 11C:
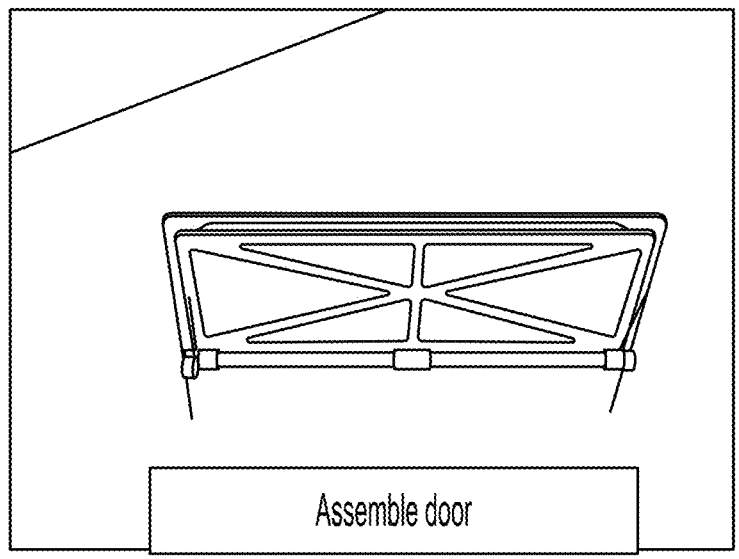
Figure 11D:
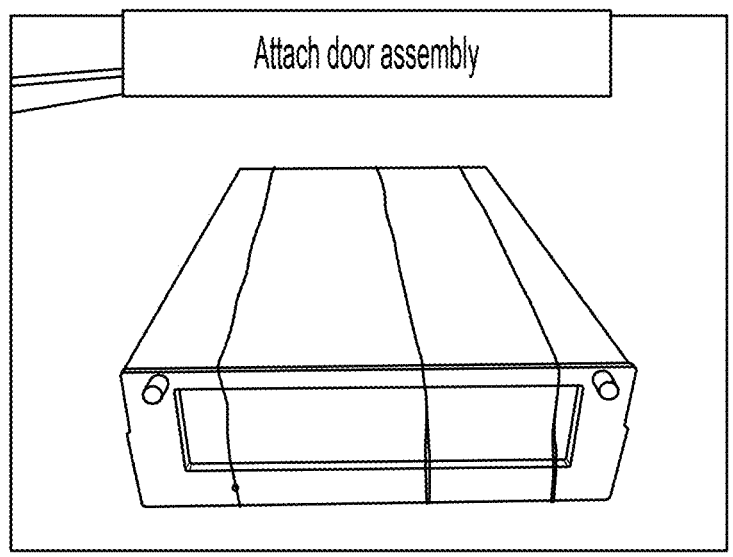
Figure 11E:
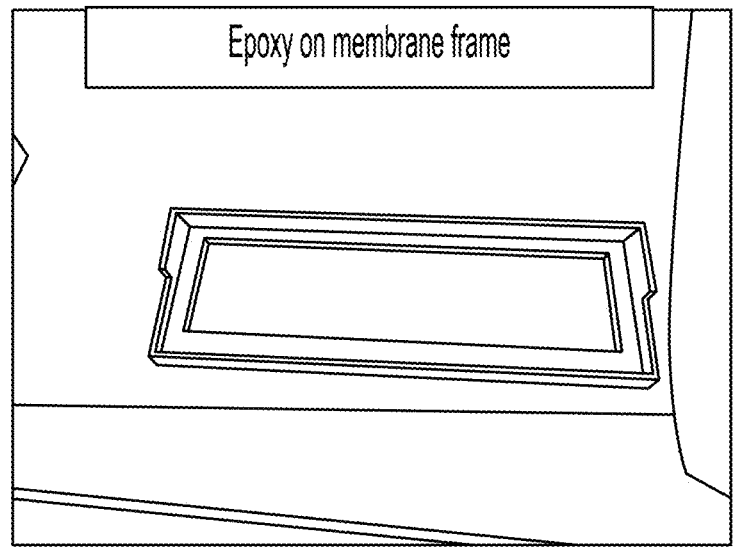
Figure 11F:
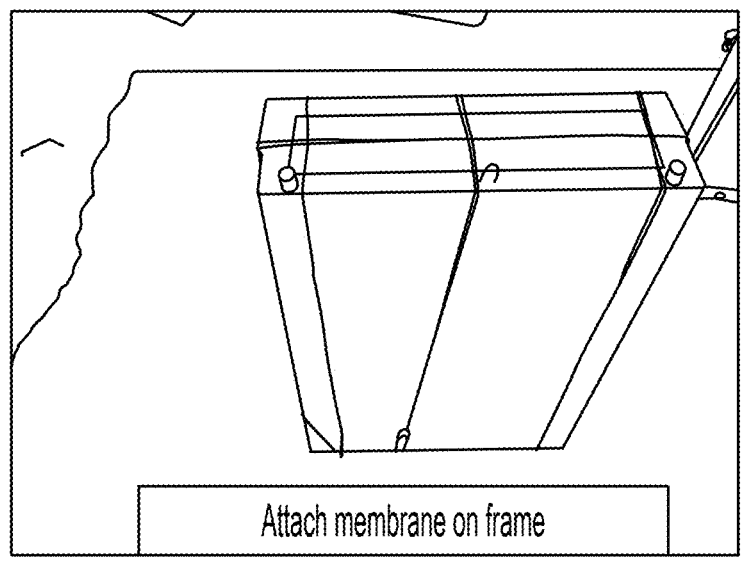
Figure 11G:
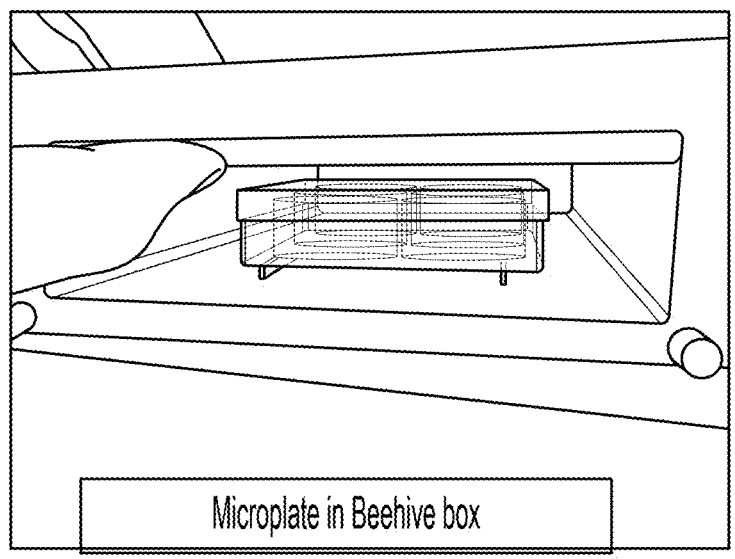

FIGS. 11A-11G provide a non-limiting example of assembly of a selectively permeable cell culture vessel storage container. A door seal is attached to a first door frame (FIG. 11A). Then, a selectively permeable membrane is attached to a second door frame (FIG. 11B). The first door frame and second door frame are then assembled (FIG. 11C), before attachment of the door to a the walls of a cell culture storage container (FIG. 11D). Then, epoxy is placed on a membrane frame (FIG. 11E), which is attached to the container depicted in FIG. 11D (FIG. 11F). A microplate may be placed inside the assembled selectively permeable cell culture vessel storage container (FIG. 11G).

Figure 12:
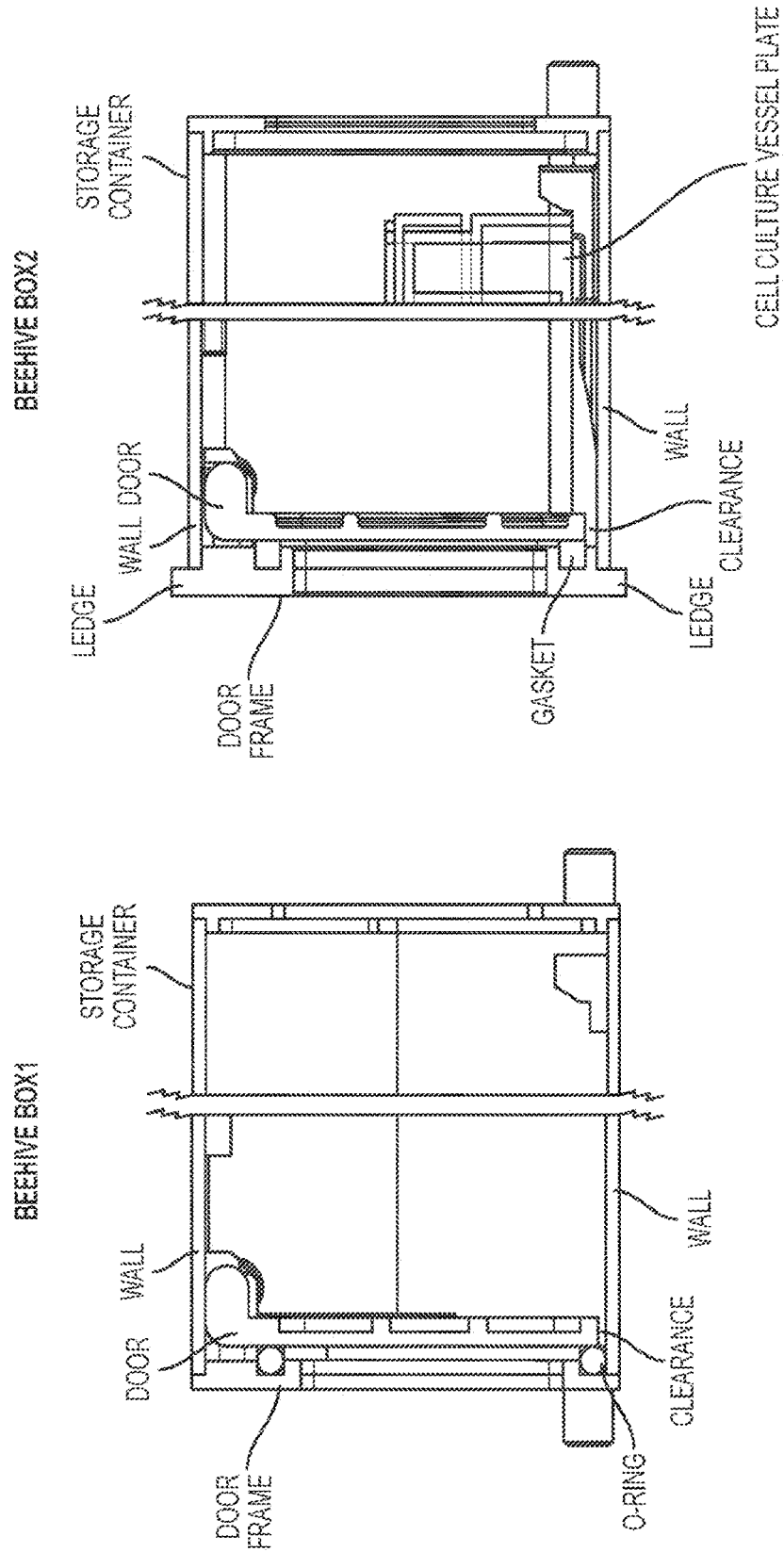
FIG. 12 is a schematic of illustrative embodiments of front/rear bond joints of selectively permeable cell culture vessel storage containers. A cross-sectional side view of two different storage container embodiments is provided. One non-limiting embodiment of a cell culture vessel storage container (e.g., Beehive Box 1) comprises a (e.g., 1 mm) clearance under the door and a (e.g., 3 mm diameter) O-ring seal. A second non-limiting embodiment of a cell culture vessel storage container (e.g., Beehive Box 2) comprises a (e.g., 2 mm) clearance under the door (e.g., a ⅛" square) flat gasket seal, and a ledge to improve bonding of the door frame to the support structure (e.g., walls of the container).

FIG. 12 is a schematic of illustrative embodiments of front/rear bond joints of selectively permeable cell culture vessel storage containers. A side view of two different embodiments is provided. One embodiment (e.g., Beehive Box 1) comprises a 1 mm clearance under the door and a 3 mm (diameter) O-ring seal. A second embodiment (e.g., Beehive Box 2) comprises a 2 mm clearance under the door, a ⅛" flat gasket seal, and a ledge to improve bonding of the door frame to the support structure (e.g., walls of the container).

Figure 13A:
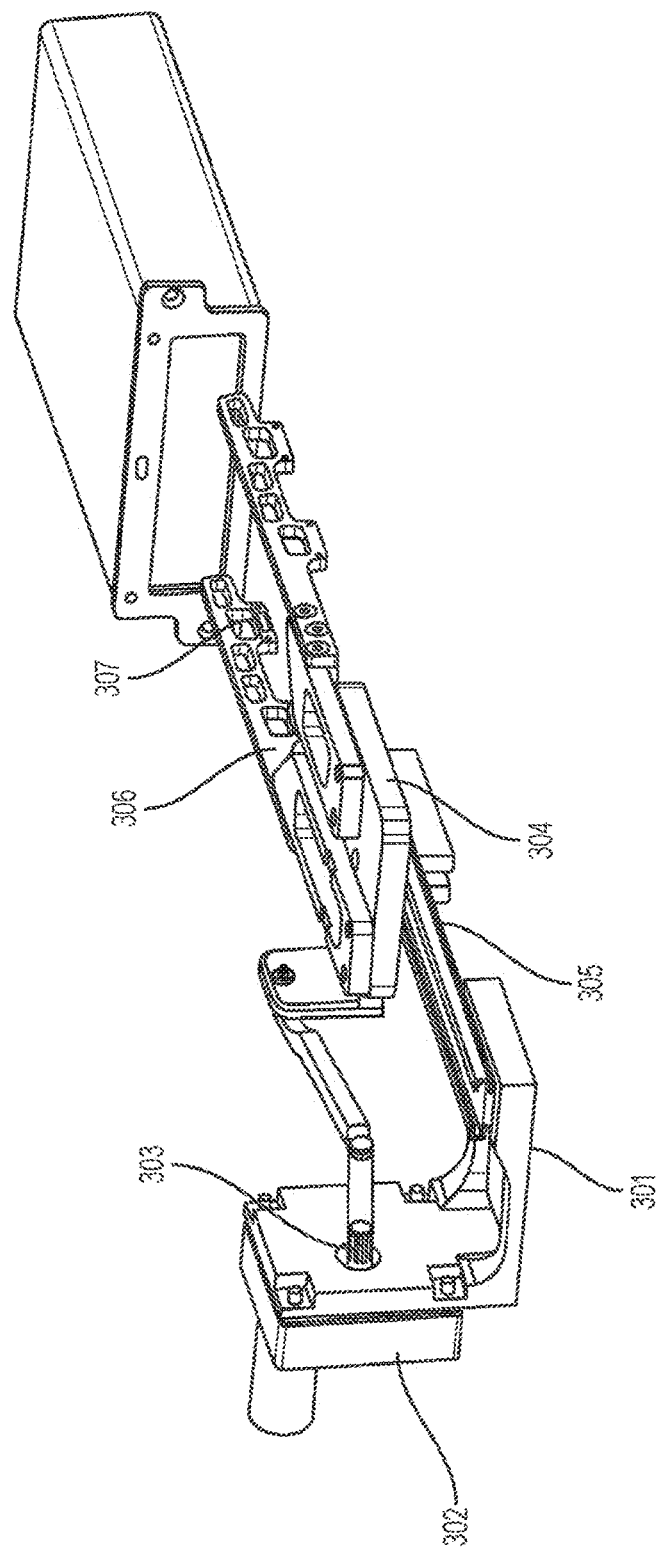
FIGS. 13A-13D are schematics of illustrative embodiments of a transfer device.

FIG. 13A depicts a rear/side angle view of a transfer device comprising a support structure (301); a motor (302) attached to the support structure (301), the motor (302) comprising a rotor (303), a plate holder (304) configured to translate along a longitudinal axis of a guide rail (305) of the support structure (301); the plate holder (304) comprises two, opposed arms (306) extending parallel to the longitudinal axis of the guide rail (305), wherein each arm comprises one or more contact surfaces (307) for engaging with the multi-well culture plate (111) (not shown).

Figure 13B:
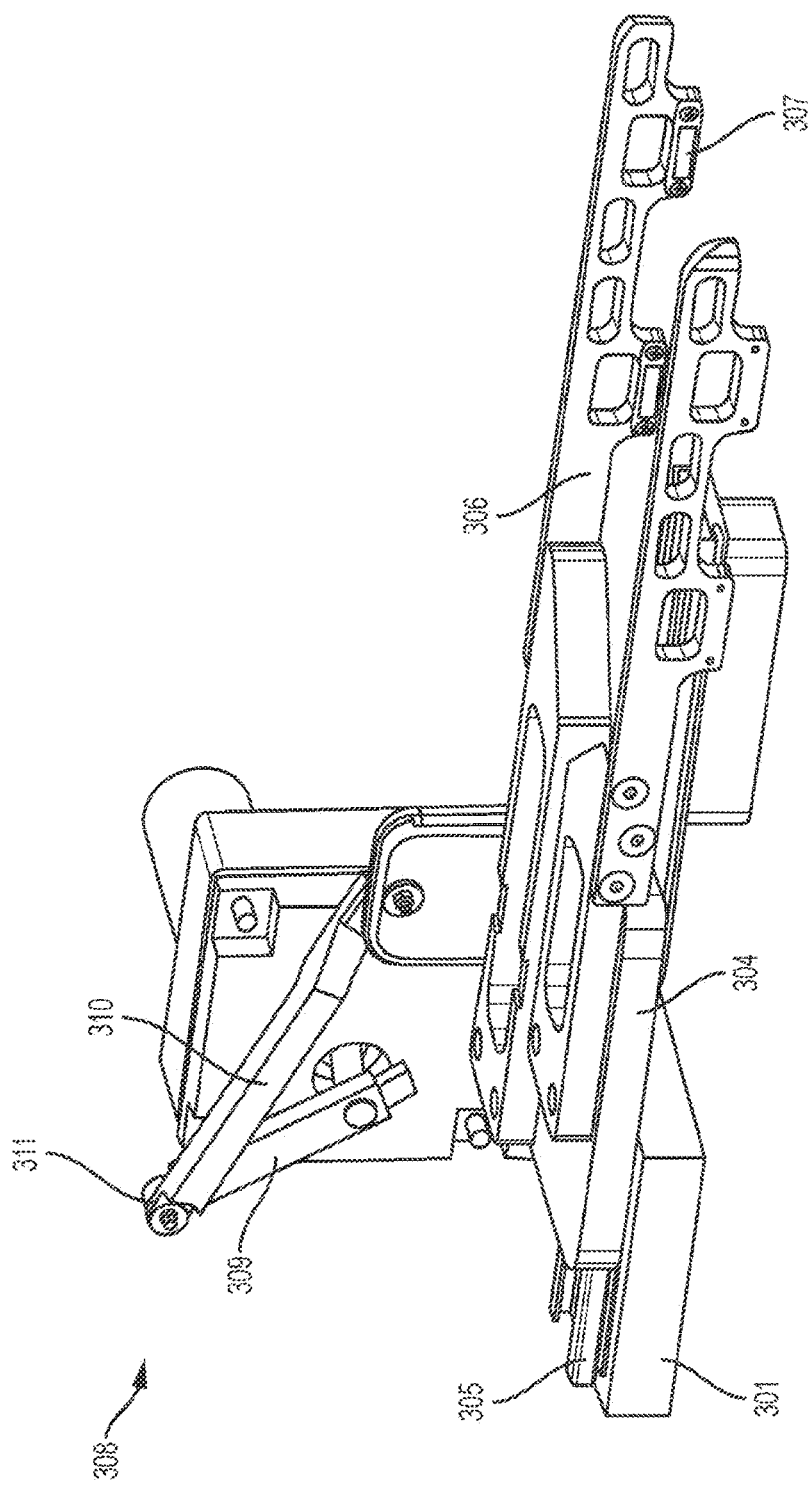

FIG. 13B depicts a view of the transfer device described in FIG. 13A from a front/side angle. A manipulator arm (308) comprising a proximal region (309) coupled to the rotor, a distal region (310) coupled to the plate holder (304) and an elbow (311) positioned between the proximal region (309) and distal region (310), wherein the manipulator arm (308) is configured to convert torque imparted through the rotor to a translational force imparted on the plate holder (304) to cause the plate holder (304) to translate along longitudinal axis of a guide rail (305).

Figure 13C:
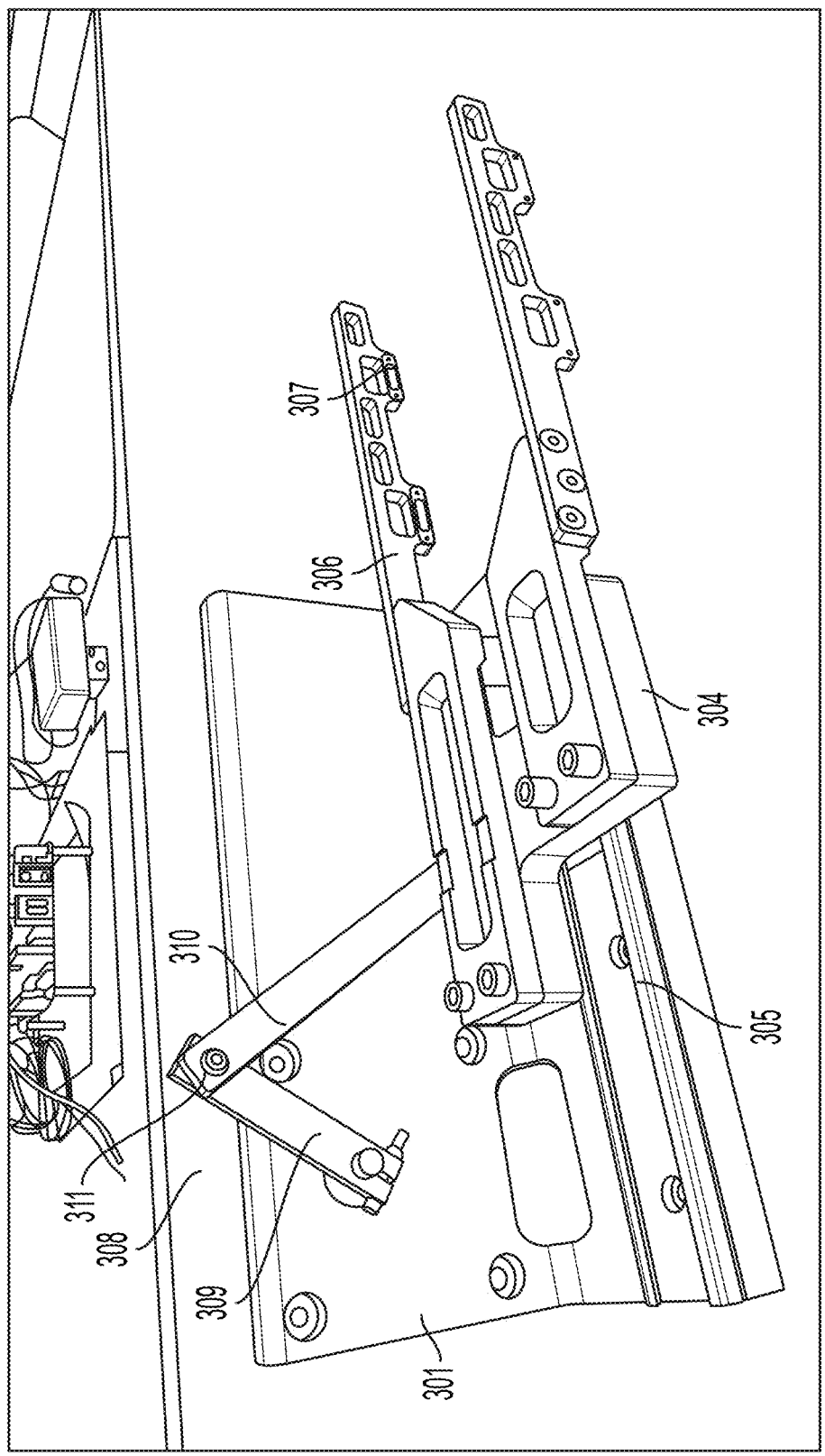

FIG. 13C depicts a view of the transfer device described in FIG. 13A from a front/side angle. A manipulator arm (308) comprising a proximal region (309) coupled to the rotor, a distal region (310) coupled to the plate holder (304) and an elbow (311) positioned between the proximal region (309) and distal region (310), wherein the manipulator arm (308) is configured to convert torque imparted through the rotor to a translational force imparted on the plate holder (304) to cause the plate holder (304) to translate along longitudinal axis of a guide rail (305).

Figure 13D:
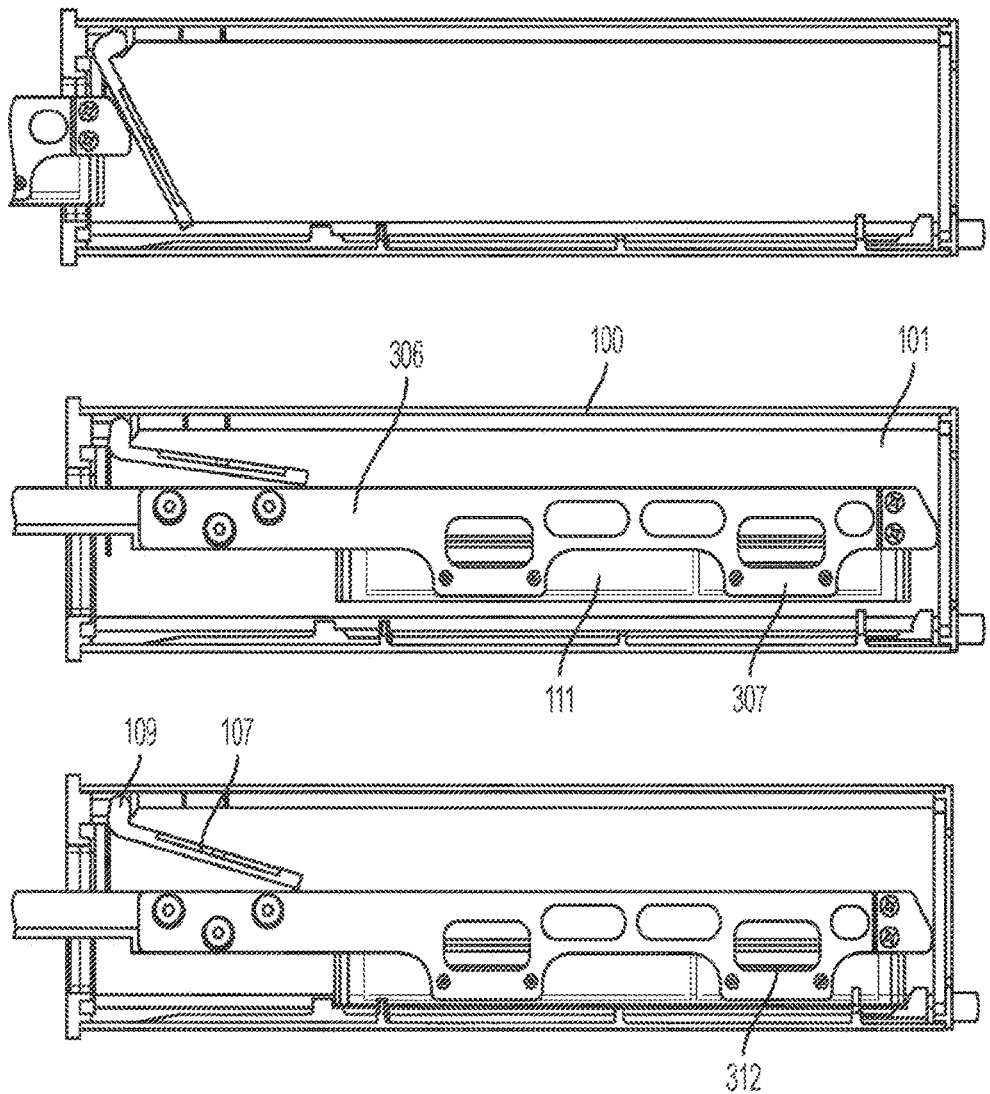

FIG. 13D is a schematic of an illustrative embodiment of a transfer device (e.g., as described in FIG. 13A) accessing the interior chamber (101) of a selectively permeable cell culture vessel storage container (100). The arms (306) of the transfer device push open the door (107) of the container via a hinge (109); the arms (306) transfer a microplate (111) on the bottom surface of the container. In some embodiments, the multi-well culture plate comprises a rectangular cuboidal body housing a plurality of cell culture wells, and wherein the set of contact surfaces (307) of the transfer device are configured for interfacing with opposite vertical surfaces (312) of the rectangular cuboidal body to hold the multi-well culture plate.

The above aspects and embodiments may be employed in any suitable combination, as the present invention is not limited in this respect.

It should be understood that aspects of the invention are described herein with reference to certain illustrative embodiments and the figures. The illustrative embodiments described herein are not necessarily intended to show all aspects of the invention, but rather are used to describe a few illustrative embodiments. Thus, aspects of the invention are not intended to be construed narrowly in view of the illustrative embodiments. In addition, it should be understood that aspects of the invention may be used alone or in any suitable combination with other aspects of the invention.

Having thus described several aspects of at least one embodiment of this invention, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. A method for culturing cells, the method comprising:
   placing cells in a multi well cell culture vessel,
   placing the cell culture vessel in a container, the container having a movable door for receiving a cell culture vessel therein, wherein a portion of at least one wall of the container comprises a gas permeable membrane that is selectively impermeable to water vapor to provide a humidified sub-environment for a cell culture therein;
   placing the cell culture container into a non-humidified temperature controlled incubator and maintaining a non-humidified environment therein;
   passing gases into the humidified sub-environment from the non-humidified temperature controlled incubator through the gas permeable membrane, and passing gases out of the humidified sub-environment into the non-humidified temperature controlled incubator through the gas permeable membrane, while preventing the passage of water vapor from the humidified sub-environment into the non-humidified temperature controlled incubator using the gas permeable membrane that is selectively impermeable to water vapor;
   storing the cell culture container in a storage rack;
   imaging the cells in the cell culture vessel in an imaging location; and
   robotically transferring the cell culture vessel through the movable door of the container to the imaging location and returning the cell culture vessel through the movable door of the container to store same.

2. The method of claim 1, wherein the gas permeable membrane is permeable to $O_2$ and $CO_2$.

3. The method of claim 1, wherein the gas permeable membrane has a thickness in a range of 0.1 μm to 200 μm.

4. The method of claim 1, wherein the gas permeable membrane is composed of polytetrafluoroethylene (PTFE), polyvinylidene fluoride (PVDF), polyethersulfone (PES), or fluorinated ethylene-propylene (FEP).

5. The method of claim 1, wherein the gas permeable membrane is hydrophobic.

6. The method of claim 1, wherein the gas permeable membrane is readily detachable.

7. The method of claim 1, wherein the movable door comprises a hinge configured to permit the movable door to move between an open position to a closed position.

8. The method according to claim 1, wherein the step of robotically transferring comprises raising and lowering the cell culture vessel to enter and exit a container and sliding the cell culture vessel to enter and exit the imaging location.

9. The method according to claim 1, wherein the imaging location includes at least one bright-field imager.

* * * * *